United States Patent [19]

Gorog nee Privitzer et al.

[11] Patent Number: 4,787,933
[45] Date of Patent: Nov. 29, 1988

[54] HERBICIDE COMPOSITIONS CONTAINING A NITRILE DERIVATIVE AS ANTIDOTE

[75] Inventors: Katalin Görög née Privitzer; Mária Kocsis née Bagyi; György Orosz; Tamás Török, all of Budapest; István László, Balassagyarmat; László Kondár, Velence; István Tóth, Miskolc; Károly Balogh, Miskolc; Tibor Bódi, Miskolc; Erzsébet Grega née Tóth, Miskolc; Zsolt Dombay, Miskolc; József Nagy, Miskolc; Csaba Pavliscsák, Sajóbábony, all of Hungary

[73] Assignee: Eszakmagyarorszagi Vegyimuvek, Sajobabony, Hungary

[21] Appl. No.: 65,265

[22] Filed: Jun. 22, 1987

[30] Foreign Application Priority Data

Jun. 26, 1986 [HU] Hungary .................. 2664/86

[51] Int. Cl.$^4$ .................. A01N 37/34; A01N 47/30
[52] U.S. Cl. .................. 71/105; 71/88; 71/94; 71/96; 71/100; 71/118; 71/120
[58] Field of Search .................. 71/105, 120

[56] References Cited

U.S. PATENT DOCUMENTS

2,960,534 11/1960 Scherer et al. .................. 71/120
4,070,389 1/1978 Martin .................. 71/120
4,309,210 1/1982 Quadranti et al. .................. 71/120

FOREIGN PATENT DOCUMENTS

0019123 2/1976 Japan .................. 71/105

Primary Examiner—Glennon H. Hollrah
Assistant Examiner—Susan P. Treanor
Attorney, Agent, or Firm—Herbert Dubno; Jonathan Myers

[57] ABSTRACT

The invention relates to a herbicide composition comprising as herbicidally active ingredient an urea derivative and/or a thiolcargamate derivative and/or a chloroacetanilide derivative together with a nitrile derivative of the general formula (I),

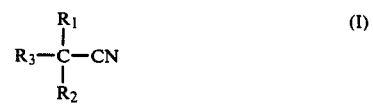

wherein
- $R_1$ and $R_2$ which are the same or different, stand for hydroger, halogen or a methyl, ethyl, allyl, vinyl, phenyl or benzyl group; or
- $R_1$ and $R_2$ together may stand for a benzylidene group; and
- $R_3$ means chlorine or a methyl, phenyl, chlorophenyl, alkoxyphenyl, chlorophenylamino, anilino, anilinomethylene, N-alkylanilinomethylene, N,N-dialkylanilinomethylene, alkoxyanilinomethylene, benzylaminomethylene, cyclohexylaminomethylene, N-alkyl-cyclohexylaminomethylene, hexamethyleniminomethylene, phthalimidomethylene, nitrophthalimidomethylene, morpholinomethylene, piperidinomethylene, $C_{1-3}$alkylaminomethylene, allylaminomethylene or di($C_{1-3}$alkyl)aminoethylene group and/or together with a cyanopyridine and/or with a benzonitrile derivative optionally mono- or polysubstituted by halogen(s) or $C_{1-3}$ alkoxy group(s) as antidote(s) in a mass ratio from 40:1 to 1:1 of the herbicidally active ingredient to the antidote nitrile derivative.

5 Claims, No Drawings

HERBICIDE COMPOSITIONS CONTAINING A NITRILE DERIVATIVE AS ANTIDOTE

FIELD OF THE INVENTION

The invention relates to a herbicide composition containing as active ingredient a urea derivative of the formula (II)

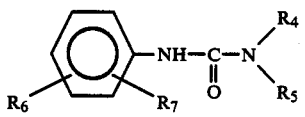

and/or a thiolcarbamate derivative of the formula (III)

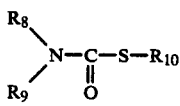

and/or a chloroacetanilide derivative of the formula (IV)

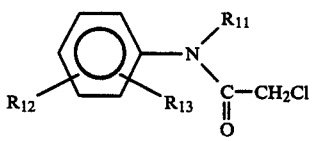

and as an antidote a nitrile derivative of the formula (I)

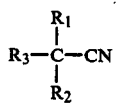

and/or a cyanopyridine and/or a benzonitrile derivative optionally mono- or polysubstituted by halogen or $C_{1-3}$ alkoxy diminishing the phytotoxicity of the active ingredient.

In the formula (I)

$R_1$ and $R_2$ which are the same or different, stand for hydrogen, halogen or a methyl, ethyl, allyl, vinyl, phenyl or benzyl group; or $R_1$ and $R_2$ together may stand for a benzylidene group; and $R_3$ means chlorine or a methyl, phenyl, chlorophenyl, alkoxyphenyl, chlorophenylamino, anilino, anilinomethylene, N-alkylanilinomethylene, N,N-dialkylanilinomethylene, alkoxyanilinomethylene, benzylaminomethylene, cyclohexylaminomethylene, N-alkyl-cyclohexylaminomethylene, hexamethyleniminomethylene, phthalimidomethylene, nitrophthalimidomethylene, morpholinomethylene, piperidinomethylene, $C_{1-3}$alkylaminomethylene, allylaminomethylene or di($C_{1-3}$alkyl)aminomethylene group.

In the formula (II)

$R_4$ and $R_5$ which are the same or different, stand for a methyl or methoxy group;

$R_6$ and $R_7$ which are the same or different, represent hydrogen, halogen, a $C_{1-3}$ alkyl or a methoxy group.

In the formula (III)

$R_8$ and $R_9$ which are the same or different, stand for a $C_{1-4}$ alkyl group or a cyclohexyl group; or $R_8$ and $R_9$ together may stand for a hexamethylene group;

$R_{10}$ is an ethyl, propyl, benzyl, chlorobenzyl, 2,3-dichlorobenzyl or a 2,3-dichloroallyl group.

In the formula (IV)

$R_{11}$ stands for an alkoxyalkyl group containing 2 to 5 carbon atoms; and $R_{12}$ and $R_{13}$ which are the same or different, stand for a methyl or ethyl group.

BACKGROUND OF THE INVENTION

The urea derivatives of the formula (II), the triolcarbamate derivatives of formula (III) and the chloroacetanilide derivatives of formula (IV) have long been known as herbicidally active agents and are widely used for plant protection.

It is known however that these active agents, when used in an effective dose for the herbicidal action, also exert a damaging action of varying extent on the cultivated plants.

In the fifties, Hoffmann recognized that some compounds such as 1,8-naphthalic acid and its salts are useful for the decrease in the phytotoxicity of these herbicides [see the U.S. Pat. Nos. 3,131,509 and 3,702,759].

Since that time, the research into antidote compounds has had an intense development.

As a result of the researches carried out in the Stauffer Chemical Company, a novel type of antidotes, i.e. the N,N-disubstituted dichloroacetamides have been recognized [see the German Pat. (DE-PS) Nos. 2,218,097 and 2,350,800]. Since then, several groups of such compounds have been developed which are useful for diminishing the phytotoxicity, although their activity is different.

The antidote effect of a newer type of compounds, i.e. dicarboxylic acid derivatives (esters and amides) is described in the Hungarian Pat. No. 176,669.

Since the mechanism of action of the phytotoxicity of the above-mentioned herbicide agents is various and contraversial and the effect of the antidotes developed up to now is varying, this research is being continued.

In addition to the esters and amines, among the dicarboxylic acid derivatives as antidotes, the dinitrile derivatives [e.g. phthalic acid dinitrile (phthalonitrile) and terephthalic acid dinitrile (terephthalonitrile)] are also mentioned as substances diminishing phytotoxicity (Hungarian Pat. No. 176,669).

Likewise, the antidote effect of dinitrile derivatives is disclosed in the U.S. Pat. No. 4,260,555 and in the Soviet Pat. No. 880,242. The structure of these compounds is rather complicated. Thus, the preparation of them is difficult and expensive.

DESCRIPTION OF THE INVENTION

Now we have found, in our research aimed at the development of antidotes that the phytotoxicity of the urea derivatives of formula (II), thiolcarbamate derivatives of the formula (III) and chloroacetanilide derivatives of the formula (IV) as herbicide agents can effectively be decreased without influencing their herbicide effects by using the nitrile derivatives of the formula (I) or cyanopyridines or benzonitriles mono- or polysubstituted by halogen or alkoxy.

In the formula (I)

$R_1$ and $R_2$ which are the same or different, stand for hydrogen, halogen or a methyl, ethyl, allyl, vinyl, phenyl, or benzyl group; or $R_1$ and $R_2$ together may stand for a benzylidene group; and $R_3$ is chlorine or a methyl, phenyl, chlorophenyl, alkoxyphenyl, chlorophenylamino, anilino, anilinomethylene, N-alkylanilinomethylene, N,N-dialkylanilinomethylene, alkoxyanilinomethylene, benzylaminomethylene, cyclohexylaminomethylene, N-alkyl-cyclohexylaminomethylene, hexamethyleniminomethylene, phthalimidomethylene, nitrophthalimidomethylene, morpholinomethylene, piperidinomethylene, $C_{1-3}$alkylaminomethylene, allylaminomethylene or a di($C_{1-3}$alkyl)aminomethylene group.

The most important compounds of the formula (I) together with the substituents as well as the physical characteristics (melting point, refractive index) of these compounds and the cyanopyridines and substituted benzonitriles are summarized in Table 1.

TABLE I

| No. | Compound | Substituents | | | Physical characteristics | |
|---|---|---|---|---|---|---|
| | | $R_1$ | $R_2$ | $R_3$ | m.p. °C. | Refractive index |
| 1 | 2 | 3 | 4 | 5 | 6 | 7 |
| 1 | Pivalonitrile | methyl | methyl | methyl | 15 | — |
| 2 | Trichloroacetonitrile | Cl | Cl | Cl | — | 1.440 |
| 3 | 4-Ethoxyphenylacetonitrile | H | H | 4-ethoxyphenyl | 39–43 | — |
| 4 | 2-(4-Ethoxyphenyl)butyronitrile | H | ethyl | 4-ethoxyphenyl | — | 1.5117 |
| 5 | 2-Phenyl-2-methylpropionitrile | methyl | methyl | phenyl | — | 1.5041 |
| 6 | 2-Phenylbutyronitrile | H | ethyl | phenyl | — | 1.5065 |
| 7 | 2-Benzyl-2-phenylbutyronitrile | ethyl | benzyl | phenyl | — | 1.5607 |
| 8 | 2-(4-Ethoxyphenyl)-2-methylpropionitrile | methyl | methyl | 4-ethoxyphenyl | 56–58 | — |
| 9 | 2,3-Diphenylacrylonitrile | benzylidene | | phenyl | 86–88 | — |
| 10 | 2-Cyanopyridine | — | — | — | 212–215 | — |
| 11 | 3-Cyanopyridine | — | — | — | 50–52 | — |
| 12 | 4-Cyanopyridine | — | — | — | 78–80 | — |
| 13 | 2-Ethyl-2-phenylbutyronitrile | ethyl | ethyl | phenyl | — | 1.5039 |
| 14 | 2-(4-Chlorophenyl)-2-ethylbutyronitrile | ethyl | ethyl | 4-chlorophenyl | 53–57 | — |
| 15 | 2-(4-Chlorophenyl)-2-methylpropionitrile | methyl | methyl | 4-chlorophenyl | — | 1.5204 |
| 16 | 2-Chlorophenylacetonitrile | H | H | 2-chlorophenyl | — | 1.5440 |
| 17 | 3-Chlorophenylacetonitrile | H | H | 3-chlorophenyl | — | 1.5437 |
| 18 | 4-Chlorophenylacetonitrile | H | H | 4-chlorophenyl | 265–267 | — |
| 19 | Diphenylacetonitrile | H | phenyl | phenyl | 71–73 | — |
| 20 | 3-Phthalimidopropionitrile | H | H | phthalimidomethylene | 153–154 | — |
| 21 | 3-(3-Nitrophthalimido)propionitrile | H | H | 3-nitrophthalimidomethylene | 132–134 | — |
| 22 | 3-(4-Nitrophthalimido)propionitrile | H | H | 4-nitrophthalimidomethylene | 136–138 | — |
| 23 | 2-Allyl-2-phenyl-4-pentenenitrile | allyl | allyl | phenyl | — | 1.5243 |
| 24 | 3-Anilinopropionitrile | H | H | anilinomethylene | 48–49 | — |
| 25 | 3-Cyclohexylaminopropionitrile | H | H | cyclohexylaminomethylene | — | 1.4737 |
| 26 | 3-Benzylaminopropionitrile | H | H | benzylaminomethylene | — | 1.5272 |
| 27 | 3-N—(Ethylcyclohexyl)aminopropionitrile | H | H | N—ethylcyclohexylaminomethylene | — | 1.4709 |
| 28 | 3-N—(Methylanilino)propionitrile | H | H | N—methylanilinomethylene | — | 1.5591 |
| 29 | 3-N—(Ethylanilino)nitrile | H | H | N—ethylanilinomethylene | — | 1.5528 |
| 30 | 3-N—(Isopropylanilino)propionitrile | H | H | N—ispropylanilinomethylene | — | 1.5418 |
| 31 | 3-Hexamethyleniminopropionitrile | H | H | hexamethyleniminomethylene | — | 1.4727 |
| 32 | 3-Morpholinopropionitrile | H | H | morpholinomethylene | — | 1.4698 |
| 33 | 3-Piperidinopropionitrile | H | H | piperidinomethylene | — | 1.4690 |
| 34 | 3-(4-Methoxyanilino)propionitrile | H | H | 4-methoxyanilinomethylene | 62–64 | — |
| 35 | 3-(2,6-Diethylanilino)- | H | H | 2,6-diethyl- | — | 1.5431 |

TABLE I-continued

| No. 1 | Compound 2 | Substituents R₁ 3 | R₂ 4 | R₃ 5 | Physical characteristics m.p. °C. 6 | Refractive index 7 |
|---|---|---|---|---|---|---|
|  | propionitrile |  |  | anilino-methylene |  |  |
| 36 | 2-Anilinoacetonitrile | H | H | Anilino | 45–47 | — |
| 37 | 2-(4-Chlorophenyl)-aminoacetonitrile | H | H | 4-chloro-phenylamino | 92–95 | — |
| 38 | Phenylacetonitrile | H | H | phenyl | — | 1.5236 |
| 39 | 2-Anilinopropionitrile | H | methyl | anilino | 86–88 | — |
| 40 | (4-Methoxyphenyl)aceto-nitrile | H | H | 4-methoxy-phenyl | — | 1.5318 |
| 41 | 3-Methylaminopropio-nitrile | H | H | methylamino-methylene | — | 1.4348 |
| 42 | 3-Diethylaminopropio-nitrile | H | H | diethylamino-methylene | — | 1.4358 |
| 43 | 3-Phthalimido-2-methylpro-pionitrile | H | H | phthalimido-methylene | 94–96 | — |
| 44 | 2-Methyl-3-(4-nitro-phthalimido)propionitrile | H | methyl | 4-nitrophthal-imidomethylene | — | — |
| 45 | 2-Methyl-3-(3-nitrophthal-imido)-propionitrile | H | methyl | 3-nitro-phthal-imidomethylene | — | — |
| 46 | 3-Anilino-2-methylpropio-nitrile | H | methyl | anilinomethylene | — | 1.4714 |
| 47 | 3-Benzylamino-2-methyl-propionitrile | H | methyl | benzylamino-methylene | — | 1.5312 |
| 48 | 3-N—Methylanilino-2-methylpropionitrile | H | methyl | N—methyl-anilino-ethylene | — | 1.5510 |
| 49 | 3-Cyclohexylamino-2-methylpropionitrile | H | methyl | ciklohexyl-aminomethylene | — | 1.4797 |
| 50 | 3-N—Ethylanilino-2-methylpropionitrile | H | methyl | N—ethylanilino-methylene | — | 1.5484 |
| 51 | 3-N—Isopropylanilino-2-methylpropionitrile | H | methyl | N—isopropyl-anilinomethylene | — | 1.5392 |
| 52 | 2-Chlorobenzonitrile | — | — | — | 44–45 | — |
| 53 | 2,4,6-Trimethoxy-benzonitrile | — | — | — | 92–94 | — |
| 54 | 3-Chlorobenzonitrile | — | — | — | 38–40 | — |
| 55 | 4-Chlorobenzonitrile | — | — | — | 91–93 | — |
| 56 | 3-(2,6-Dimethylanilino)-propionitrile | H | H | 2,6-dimethyl-anilinomethylene | — | 1.4832 |
| 57 | 3-(6-Ethyl-2-methyl-anilino)propionitrile | H | H | 6-ethyl-2-methylanilino-methylene | — | 1.4916 |
| 58 | 3-(n-Propylamino)-propionitrile | H | H | propylamino-methylene | — | 1.4354 |
| 59 | 3-Allylaminopropio-nitrile | H | H | allylamino-methylene | — | 1.4547 |

For the preparation of the nitrile derivatives of the formula (I), several processes are known in the literature.

Pivalonitrile, item No. 1 in Table I, which is the simplest derivative can be prepared by reacting pivalic acid with ammonia under dehydrating conditions [see the German Pat. No. 3,216,382]. However, pivalonitrile (trimethylacetoritrile) can also be prepared by reacting the appropriate olefin, i.e. isobutylene with hydrogen cyanide at an elevated temperature [see the U.S. Pat. No. 2,455,995].

According to K. Rokrig et al., 4-ethoxy-phenylacetonitrile is prepared by reacting 4-ethoxybenzyl chloride with sodium cyanide (Org. Synth. Coll. Vol. IV., p. 576).

M. Lora et al. transformed pivalic acid to the acid chloride by using thionyl chloride in the first step, and the acid chloride was then reacted with ammonia to give pivalic acid amide. This amide was reacted with phosphorus pentoxide in a solvent to yield pivalonitrile (Anales Real. Soc. Espan. 48B, p. 414–420).

Among the urea derivatives of the formula (II), the phytotoxicity of which is decreased by the nitrile derivatives of the formula (I), 3-(4-chlorophenyl)-1,1-dimethylurea (monuron), 3-(3,4-dichlorophenyl)-1,1-dimethylurea (diuron), 3-(3-chloro-4-methoxyphenyl)-1,1-dimethylurea (metoxuron), 3-(3-chloro-4-methylphenyl)-1,1-dimethylurea (chlortoluron), 3-(4-chlorophenyl)-1-methyl-1-methoxyurea (monoliruror), 3-(3,4-dichlorophenyl)-1-methyl-1-methoxyurea (linuron), 3-(4-bromophenyl)-1-methyl-1-methoxyurea (metobromuron), 3-(4-bromo-3-chlorophenyl)-1-methyl-1-methoxyurea (chlorbromuron), 3-[3-(trifluormethyl)-phenyl]-1,1-dimethylurea (fluometuron), 1,1-dimethyl-3-phenylurea (fenuron) and 1,1-dimethyl-3-(4-isopropylphenyl)urea (isoproturon) are well known substances.

Among the thiolcarbamate derivatives of the formula (III), for which the nitrile derivatives of the formula (I) are useful antidotes, the following compounds are well known and widely used in the practice: S-ethyl N,N-diisobutylthiolcarbamate (butylate), S-ethyl N,N-di(n-propyl)thiolcarbamate (EPTC), S-ethyl N,N-hexamethylenethiolcarbamate (molinate), S-ethyl N-cyclohexyl-N-ethylthiolcarbamate (cycloate), S-propyl N,N-di(n-propyl)thiolcarbamate (vernolate), S-(2,3-dichloroallyl) N,N-diisopropylthiolcarbamate (diallate), S-(4-chlorobenzyl)-N,N-diethylthiolcarbamate (thiobencarb) and S-benzyl N,N-di(secundary-butyl)-thiolcarbamate.

Among the chloroacetanilide derivatives of the formula (IV), the phytotoxicity of which is diminished by the nitrile derivatives of the formula (I), the most known substances are as follows:

2-chloro-2',6'-diethyl-N(methoxymethyl)acetanilide (alachlor),
2-chloro-2'-ethyl-6'-methyl-N-(ethoxymethyl)acetanilide (acetochlor),
2-chloro-2'-ethyl-6'-methyl-N-(1-methyl-2-methoxyethyl)acetanilide (metolachlor) and
2-chloro-2',6'-diethyl-N-(butoxymethyl)acetanilide (butachlor).

As clearly seen from Table I, the nitrile derivatives of the formula (I) are partly solids and partly liquids.

The solid nitrile derivatives can be formulated e.g. to wettable powders (WP) by using the common additives of plant protective compositions (carriers, surface active agents), which may be applied together with herbicide compositions of a similar formulation in the form of tank mixtures.

Both the liquid and solid nitrile derivatives can be formulated e.g. to stable emulsifiable concentrates by selecting a suitable solvent and emulsifying agent which may be mixed with herbicide emulsifiable concentrates and may be applied in the form of tank mixtures.

The nitrile derivatives may also be formulated together with the urea derivatives and/or thiolcarbamate derivatives and/or chloroacetanilide derivatives.

SPECIFIC EXAMPLES

The formulations containing the nitrile derivatives alone as well as the compositions formulated together with herbicide agents are illustrated in detail in the following non-limiting Examples.

EXAMPLE 1

Composition of an emulsifiable concentrate containing 2,3-diphenylacrylonitrile (compound No. 9) as antidote

|  | % by mass |
| --- | --- |
| 2,3-Diphenylacrylonitrile | 10 |
| Atlox 4857B emulsifying agent | 10 |
| Xylene | 80 |

EXAMPLE 2

Composition of an emulsifiable concentrate containing trichloroacetonitrile (compound No. 2) as antidote

|  | % by mass |
| --- | --- |
| Trichloroacetonitrile | 20 |
| Emulsogen IP 400 | 10 |
| Xylene | 70 |

EXAMPLE 3

Composition of an emulsifiable concentrate containing 2-benzyl-2-phenylbutyronitrile (compound No. 7) as antidote

|  | % by mass |
| --- | --- |
| 2-Benzyl-2-phenylbutyronitrile | 30 |
| Atlox 4857B emulsifying agent | 10 |
| Xylene | 60 |

Emulsifiable concentrates with a similar composition may be prepared by using 4-chlorophenylacetonitrile (compound No. 18), 2-(4-chlorophenyl)-2-methylpropionitrile (compound No. 15), or 2-(4-ethoxyphenyl)-butyronitrile (compound No. 4) as antidotes.

EXAMPLE 4

Composition of an emulsifiable concentrate containing pivaloritrile (compound No. 1) as antidote

|  | % by mass |
| --- | --- |
| Pivalonitrile | 50 |
| Emulsogen IP 400 emulsifying agent | 10 |
| Xylene | 40 |

EXAMPLE 5

Composition of an emulsifiable concentrate containing 2-cyanopyridine (compound No. 10) as antidote

|  | % by mass |
| --- | --- |
| 2-Cyanopyridine | 50 |
| Emulsogen IP 400 emulsifying agent | 10 |
| Xylene | 40 |

EXAMPLE 6

Composition of a wettable powder containing 2-methyl-2-phenylpropionitrile (compound No. 5) as antidote

|  | % by mass |
| --- | --- |
| 2-Methyl-2-phenylpropionitrile | 20 |
| Arkopon T | 5 |
| Dispergiermittel SI dispersing agent | 5 |
| Zeolit 424 carrier | 70 |

EXAMPLE 7

Composition of a wettable powder containing (4-ethoxyphenyl)acetonitrile (compound No. 3) as antidote

|  | % by mass |
| --- | --- |
| (4-Ethoxyphenyl)acetonitrile | 40 |
| Arkopon T | 5 |
| Dispergiermittel SI dispersing agent | 5 |
| Zeolit 424 carrier | 50 |

EXAMPLE 8

Composition of a wettable powder containing 3-cyanopyridine (compound No. 11) as antidote

|  | % by mass |
| --- | --- |
| 3-Cyanopyridine | 70 |
| Arkopon T | 5 |
| Dispergiermittel SI dispersing agent | 5 |

-continued

| | % by mass |
|---|---|
| Zeolex 424 carrier | 20 |

EXAMPLE 9

Composition of a water-soluble concentrate (WSC) containing pivalonitrile (compound No. 1) as antidote

| | % by mass |
|---|---|
| Pivalonitrile | 90 |
| Emulsogen IP 400 emulsifying agent | 10 |

EXAMPLE 10

Composition of an emulsifiable concentrate containing 4-cyanopyridine (compound No. 12) as antidote

| | % by mass |
|---|---|
| 4-Cyanopyridine | 10 |
| Atlox 4857B emulsifying agent | 10 |
| Chlorobenzene | 80 |

EXAMPLE 11

Composition of an emulsifiable concentrate containing 2-(4-ethoxyphenyl)-2-methylpropionitrile (compound No. 8) as antidote

| | % by mass |
|---|---|
| 2-(4-Ethoxyphenyl)-2-methylpropionitrile | 40 |
| Atlox 4857B emulsifying agent | 15 |
| Xylene | 45 |

The nitrile derivatives of the formula (I) can be well formulated together with the urea derivatives of the formula (II) and/or the thiolcarbamate derivatives of the formula (III) and/or with chloroacetanilide derivatives of the formula (IV) as illustrated in the following Examples.

EXAMPLE 12

Composition of a wettable powder containing an antidote and an urea as active ingredient

| | % by mass |
|---|---|
| N—(3,4-Dichlorphenyl)-N'—methyl-N'—methoxyurea | 50 |
| Trichloroacetonitrile (compound No. 2) | 25 |
| Amorphous silicic acid carrier | 20 |
| Fatty alcohol sulfonate | 2.5 |
| Sodium lignin sulfonate | 2.5 |

The above components are homogenized in a powder mixer, then finely ground in an Alpine 100 LU type laboratory mill. The floatability of the composition amounts to 88%.

EXAMPLE 13

Composition of an emulsifiable concentrate containing an antidote and a thiolcarbamate as active ingredient

| | % by mass |
|---|---|
| S—Ethyl N,N—di(n-propyl)thiolcarbamate | 64.8 |
| 2-Ethyl-2-phenylbutyronitrile (compound No. 13) | 10.0 |
| Atlox 4857B emulsifying agent | 4.3 |
| Atlox 3400 B emulsifying agent | 2.9 |
| Kerosine | 18.0 |

EXAMPLE 14

Composition of an emulsifiable concentrate containing an antidote and a thiolcarbamate as active ingredient

| | % by mass |
|---|---|
| S—Propyl N,N—di(n-propyl)thiolcarbamate | 67.5 |
| Trichloroacetonitrile (compound No. 2) | 10.0 |
| Tensiofix AS emulsifying agent | 4.3 |
| Tensiofix IS emulsifying agent | 2.9 |
| Kerosine | 15.3 |

EXAMPLE 15

Composition of a wettable powder containing an antidote and an urea as active ingredient

| | % by mass |
|---|---|
| 1,1-Dimethyl-3-phenylurea | 50 |
| 3-Cyanopyridine (compound No. 11) | 10 |
| Zeolit 424 carrier | 20 |
| Siliceous earth carrier | 20 |
| Netzer IS wetting agent | 2 |
| Dispergiermittel | 3 |
| Sulfite waste powder | 5 |

The above components are homogenized in a powder mixer, then finely ground in an Alpine 100 LU type laboratory mill. The floatability of the composition amounts to 88%.

EXAMPLE 16

Composition of a wettable powder containing an antidote and an urea as active ingredient

| | % by mass |
|---|---|
| 3-(3,4-Dichlorophenyl)-1,1-dimethylurea | 40 |
| 2,3-Diphenylacrylonitrile (compound No. 9) | 40 |
| Zeolit 424 carrier | 12 |
| Netzer IS wetting agent | 1.5 |
| Dispergiermittel | 2.5 |
| Sulfite waste powder | 4.0 |

The above components are treated as described in Example 15 to give a powder composition with a floatability of 82.5%.

EXAMPLE 17

Composition of a wettable powder containing an antidote and an urea as active ingredient

| | % by mass |
|---|---|
| 1,1-Dimethyl-3-[(3-(trifluoromethyl)- | 50 |

-continued

|  | % by mass |
|---|---|
| phenyl]-urea |  |
| 4-Cyanopyridine (compound No. 12) | 25 |
| Zeolit 424 carrier | 15 |
| Netzer IS | 2 |
| Dispergiermittel | 3 |
| Sulfite waste powder | 5 |

The above components are treated as described in Example 15 to give a powder composition with a floatability of 86.4%.

EXAMPLE 18

Composition of a wettable powder containing an antidote and an urea as active ingredient

|  | % by mass |
|---|---|
| 3-(3,4-Dichlorophenyl)-1-methyl-1-methoxyurea | 48 |
| Premix containing pivalonitrile | 20 |
| Siliceous earth carrier | 22 |
| Netzer IS wetting agent | 2 |
| Dispergiermittel | 3 |
| Sulfite waste powder | 5 |

The above components are treated as described in Example 15 to give a powder composition with a floatability of 76%.

The premix containing the above antidote was prepared in such a way that 2 parts by mass of pivalonitrile (compound No. 1) as antidote were dissolved in 5 parts by mass of dichloromethane as solvent, then the thus-obtained solution was sprayed onto 18 parts by mass of Sipermat 50 synthetic silicate carrier under stirring, then the solvent was evaporated at 50° C.

EXAMPLE 19

Composition of a wettable powder containing an antidote and an urea as active ingredient

|  | % by mass |
|---|---|
| 3-(4-Bromo-3-chlorophenyl)-1-methyl-1-methoxyurea | 50 |
| Premix containing 2-benzyl-2-phenylbutyronitrile | 25 |
| Siliceous earth carrier | 15 |
| Netzer IS wetting agent | 2 |
| Dispergiermittel | 3 |
| Sulfite waste powder | 5 |

The above components are treated as described in Example 15 to give a powder composition with a floatability of 78.4%.

The premix containing the above antidote was prepared in such a way that 5 parts by mass of 2-benzyl-2-phenylbutyronitrile (compound No. 7) as antidote were dissolved in 5 parts by mass of dichloromethane, then the thus-obtained solution was sprayed onto 20 part by mass of Sipermat 50 synthetic silicate carrier and the solvent was evaporated at 50° C.

EXAMPLE 20

Composition of an emulsifiable concentrate containing an antidote and an urea as active ingredient

|  | % by mass |
|---|---|
| 1,1-Dimethyl-3-phenylurea | 18 |
| Pivalonitrile (compound No. 1) | 2 |
| Emulsogen IP 400 emulsifying agent | 6.4 |
| Emulsogen EL 400 emulsifying agent | 1.6 |
| 1:1 mixture of xylene with dichloromethane | 72.0 |

EXAMPLE 21

Composition of an emulsifiable concentrate containing an antidote and an urea as active ingredient

|  | % by mass |
|---|---|
| 3-(4-Bromo-3-chlorophenyl)-1-methyl-1-methoxyurea | 35 |
| 4-Ethoxyphenylacetonitrile (compound No. 3) | 5 |
| Emulsogen IP 400 emulsifying agent | 7.2 |
| Emulsogen EL 400 emulsifying agent | 0.8 |
| 2:2:1 mixture of xylene with dichloromethane and dimethylformamide | 52.0 |

EXAMPLE 22

Composition of an emulsifiable concentrate containing an antidote and an urea as active ingredient

|  | % by mass |
|---|---|
| 3-(4-Bromophenyl)-1-methyl-1-methoxyurea | 24 |
| 2-(4-Chlorophenyl)-2-ethylbutyronitrile (compound No. 14) | 3 |
| Emulsogen IP 400 emulsifying agent | 6.4 |
| Emulsogen EL 400 emulsifying agent | 1.6 |
| 2:2:1 mixture of xylene with dichloromethane and dimethylformamide | 62.0 |

EXAMPLE 23

Composition of an emulsifiable concentrate containing an antidote and an urea as active ingredient

|  | % by mass |
|---|---|
| 1,1-Dimethyl-3-[3-(trifluoromethyl)-phenyl]-urea | 23 |
| 3-Cyanopyridine (compound No. 11) | 2 |
| Emulsogen IP 400 emulsifying agent | 6.4 |
| Emulsogen EL 400 emulsifying agent | 1.6 |
| 1:1 mixture of xylene with dimethylformamide | 67.0 |

EXAMPLE 24

Composition of an emulsifiable concentrate containing an antidote and a chloroacetanilide as active ingredient

|  | % by mass |
|---|---|
| 2-Chloro-2',6'-diethyl-N—methoxymethylacetanilide | 35 |
| 2-(4-Chlorophenyl)-2-ethylbutyronitrile | 5 |

-continued

| | % by mass |
|---|---|
| (compound No. 14) | |
| Emulsogen IP 400 emulsifying agent | 6.4 |
| Emulsogen EL 400 emulsifying agent | 1.6 |
| 3:1 mixture of Aromatol with dimethylformamide | 52.0 |

EXAMPLE 25

Composition of an emulsifiable concentrate containing antidote with a chloroacetanilide and an urea as active ingredients

| | % by mass |
|---|---|
| 2-Chloro-2',6'-diethyl-N—methoxymethylacetanilide | 32 |
| 3-(4-Bromophenyl)-1-methyl-1-methoxyurea | 15 |
| Pivalonitrile (compound No. 1) | 3 |
| Emulsogen IP 400 emulsifying agent | 7.2 |
| Emulsogen EL 400 emulsifying agent | 0.8 |
| 2:2:1 mixture of xylene with dichloromethane and dimethylformamide | 42 |

EXAMPLE 26

Composition of an emulsifiable concentrate containing an antidote with a chloroacetanilide and an urea as active ingredients

| | % by mass |
|---|---|
| 2-Chloro-2',6'-diethyl-N—methoxymethylacetanilide | 31 |
| 3-(4-Bromo-3-chlorophenyl)-1-methyl-1--methoxyurea | 15 |
| 3-Cyanopyridine (compound No. 11) | 2 |
| Emulsogen IP 400 emulsifying agent | 7.2 |
| Emulsogen EL 400 emulsifying agent | 0.8 |
| 1:1 mixture of cyclohexanone with Aromatol | 44 |

EXAMPLE 27

Composition of an emulsifiable concentrate containing an antidote and a thiolcarbamate as active ingredient

| | % by mass |
|---|---|
| S—Ethyl N,N—diisobutylthiolcarbamate | 90.0 |
| 2-(4-Ethoxyphenyl)butyronitrile (compound No. 4) | 1.0 |
| Atlox 3400 B emulsifying agent | 2.0 |
| Atlox 4857B emulsifying agent | 4.0 |
| Kerosine | 3.0 |

EXAMPLE 28

Composition of a granulate containing an antidote and a thiolcarbamate as active ingredient

| | % by mass |
|---|---|
| S—Ethyl N,N—hexamethylenethiolcarbamate | 5.0 |
| 3-Cyclohexylaminopropionitrile (compound No. 25) | 3.0 |
| Calcined siliceous earth granulate carrier | 92.0 |

The above thiolcarbamate active ingredient and the antidote are dissolved in 10% by mass of dichloromethane and sprayed onto the carrier in a rotary granulating equipment under stirring, then the solvent is evaporated at 50° C. to give a granulate with a particle size of 0.2 to 1.0 mm.

EXAMPLE 29

Composition of a suspension (suspendable) concentrate containing an antidote with a thiolcarbamate and an urea as active ingredients

| | % by mass |
|---|---|
| S—Ethyl N—cyclohexyl-N—ethylthiolcarbamate | 40.0 |
| 3-(3,4-Dichlorophenyl)-1,1-dimethyl urea | 40.0 |
| 3-Phthalimidopropionitrile (compound No. 20) | 5.0 |
| Atlox 4896 B emulsifying agent | 6.0 |
| Atlox 4857 B emulsifying agent | 2.0 |
| Aqueous thickening solution of 2% by mass of a polysaccharide | 7.0 |

The tiolcarbamate active ingredient and the emulsifying agents are homogenized by stirring, then the urea active ingredient and the antidote are suspended in the mixture under stirring. The thus-obtained coarse disperse system is finely ground in a laboratory pearl mill and then homogenized with the thickening solution to give a suspension (suspendable) concentrate with a particle size lower than $10\mu$ (in 92%) and having a floatability of 88.2%.

EXAMPLE 30

Composition of an emulsifiable concentrate containing an antidote and a thiolcarbamate active ingredient

| | % by mass |
|---|---|
| S—(2,3-Dichloroallyl) N,N—diisopropylthiolcarbamate | 40.0 |
| 4-Methoxyphenylacetonitrile (compound No. 40) | 4.0 |
| Atlox 3400 B emulsifying agent | 2.2 |
| Atlox 4857 B emulsifying agent | 3.8 |
| 4:1 mixture of xylene with isophorone | 50.0 |

EXAMPLE 31

Composition of an emulsifiable concentrate containing an antidote with a thiolcarbamate and a chloroacetanilide as active ingredients

| | % by mass |
|---|---|
| S—(4-Chlorobenzyl) N,N—diethylthiolcarbamate | 75.0 |
| 2-Chloro-2'-ethyl-6'-methyl-N—ethoxymethylacetanilide | 5.0 |
| 3-Cyclohexylamino-2-methylpropionitrile (compound No 49) | 2.0 |
| Tensiofix AS emulsifying agent | 2.5 |
| Tensiofix IS emulsifying agent | 5.5 |
| Xylene | 10.0 |

EXAMPLE 32

Composition of a wettable powder containing an antidote and an urea as active ingredient

|  | % by mass |
|---|---|
| 3-(3,4-Dichlorophenyl)-1,1-dimethylurea | 80.0 |
| 4-Chlorophenylacetonitrile (compound No. 18) | 2.0 |
| Netzer IS wetting agent | 2.0 |
| Dispergiermittel 1494 dispersing agent | 4.0 |
| Wessalon S carrier | 12.0 |

The above components are treated as described in Example 15 to give a powder composition with a floatability of 86.4%.

EXAMPLE 33

Composition of an emulsifiable concentrate containing an antidote with an urea and a chloroacetanilide as active ingredients

|  | % by mass |
|---|---|
| 2-Chloro-2'-ethyl-6'-methyl-N—(1-methyl-2-methoxyethyl)acetanilide | 60.0 |
| 3-(3-Chloro-4-methoxyphenyl)-1,1-dimethylurea | 5.0 |
| 3-N—Isopropylanilino-2-methylpropionitrile (compound No. 51) | 5.0 |
| Tensiofix AS emulsifying agent | 6.5 |
| Tensiofix IS emulsifying agent | 1.5 |
| 1:1 mixture of xylene with cyclohexanone | 22.0 |

EXAMPLE 34

Composition of an equeous suspension (suspendable) concentrate containing an antidote and an urea as active ingredient

|  | % by mass |
|---|---|
| 3-(3-Chloro-4-methylphenyl)-1,1-dimethylurea | 46.0 |
| 2-Chlorobenzonitrile (compound No. 52) | 4.0 |
| Atlox 4853 B emulsifying agent | 5.0 |
| Atlox 4896 B emulsifying agent | 3.0 |
| Water | 35.0 |
| Aqueous thickening solution of 2% by mass of a polysaccharide | 7.0 |

The emulsifying agents are dissolved in the water, then the urea active ingredient and the antidote are suspended in the solution. Thereafter, the coarse disperse system is finely ground in a laboratory pearl mill and then homogenized with the thickening solution to give an aqueous suspension concentrate with a particle size lower than 10μ (in 93.6%) and having a floatability of 91.4%.

EXAMPLE 35

Composition of a wettable powder containing an antidote and an urea as active ingredient

|  | % by mass |
|---|---|
| 1,1-Dimethyl-3-(4-isopropylphenyl)urea | 72.0 |
| 2,4,6-Trimethoxybenzonitrile (compound No. 53) | 8.0 |
| Netzer IS wetting agent | 2.5 |
| Dispergiermittel 1494 dispersing agent | 3.5 |
| Ultrasyl VN 3 carrier | 14.0 |

The above components are treated as described in Example 15 to give a powder composition with a floatability of 87.2%.

EXAMPLE 36

Composition of a wettable powder containing an antidote and an urea as active ingredient

|  | % by mass |
|---|---|
| 3-(4-Chlorophenyl)-1,1-dimethylurea | 76.0 |
| 2-(4-Chlorophenylamino)acetonitrile (compound No. 37) | 4.0 |
| Netzer IS wetting agent | 2.0 |
| Dispergiermittel 1494 dispersing agent | 4.0 |
| Ultrasyl VN 3 carrier | 14.0 |

The above components are treated as described in Example 15 to give a powder composition with a floatability of 85.9%.

EXAMPLE 37

Composition of an emulsifiable concentrate containing an antidote and a chloroacetanilide as active ingredient

|  | % by mass |
|---|---|
| 2-Chloro-2',6'-diethyl-N—butoxymethylacetanilide | 78.0 |
| 2-Methyl-2-phenylpropionitrile (compound No. 5) | 2.0 |
| Tensiofix AS emulsifying agent | 3.6 |
| Tensiofix IS emulsifying agent | 2.4 |
| 1:1 mixture of xylene with dimethylformamide | 14.0 |

The auxiliary materials used in the above formulation Examples were as follows:

Emulsogen: a mixture of calcium dodecylbenzenesulfonate with fatty acid polyglycol esters (product of Hoechst)

Netzer: sodium alkylsulfonate (product of Hoechst)

Arkopon T: sodium oleylmethyltauride (product of Hoechst)

Dispergiermittel: a forecondensate of cresol and formaldehyde (product of Hoechst)

Atlox: a mixture of calcium dodecylbenzenesulfonate with poly(oxyethylene)alkylphenols (product of Atlas Chemie)

Tensiofix: octylphenyol polyglycol ether or nonylphenol polyglycol ether, respectively (product of Tensia)

Zeolex: a synthetic silicate carrier (product of Zeofinn Org. Hamine)

Wessalon S: a synthetic silicate carrier (product of Degussa)

Ultrasyl VN 3: a synthetic silicate carrier (product of Degussa)

Aromatol: a solvent mixture containing 98% of aromatic compounds with a boiling point of 145° to 190° C. (product of the Dunai Köolajipari Vállalat) (Duna Petroleum Industry Comp.).

The phytotoxicity decreasing effect of the nitrile derivatives of the formula (I) were investigated both in greenhouse as well as in field experiments.

During our inventigations, the percentage value of sprouting of the cultivated plant, the damaging effect observed on the cultivated plant and the herbicide action were measured by using the internationally accepted EWRC scores. These data are summarized in Table II.

TABLE II

| EWRC score | Phytotoxic symptoms observed on cultivated plants | General appearance of | Herbicide effect % |
|---|---|---|---|
| 1 | none | excellent | 100 |
| 2 | very mild | very good | 98 |
| 3 | mild symptoms | good | 95 |
| 4 | strong but transient symptoms, decrease in crop | satisfactory | 90 |
| 5 | symptoms of unknown origin | problematic | 82 |
| 6 | observable harmful symptoms | unsatisfactory | 70 |
| 7 | symptoms of a strong damage | poor | 55 |
| 8 | symptoms of a very strong damage | very poor | 30 |
| 9 | total perishment | unsuitable | 0 |

EXAMPLE 38

Study of the antidote effect on urea-type herbicides in greenhouse tests

These tests were carried out in cultivating pots with 4-fold repetitions. The pots of 14 cm in diameter were filled with soil, then 10 maize grains each were sown in the pots and covered with a soil layer of 4 cm in height. Then, the pots were treated with the appropriate amount of an urea-type herbicide and the formulated antidote. The plants were cultivated in a greenhouse and sprinkled when necessary. The sprouting plants were evaluated at the end of the fourth week following the sowing. The percentage of the sprouting and the EWRC score of the maize were determined.

TABLE III

| Nitrile compound No. | Herbicide agent | Antidote kg/hectare | Herbicide kg/hectare | Sprouting % | EWRC score |
|---|---|---|---|---|---|
| 1 | Fenuron | 2.5 | 2.0 | 93.3 | 1 |
| 1 | Fenuron | 2.5 | 1.0 | 93.3 | 2 |
| 1 | Fenuron | 0.5 | 2.0 | 96.6 | 1 |
| 1 | Fenuron | 0.5 | 1.0 | 93.3 | 1 |
| 2 | Fenuron | 0.5 | 2.0 | 95.0 | 2 |
| 11 | Fenuron | 0.5 | 2.0 | 93.0 | 2 |
| 1 | Linuron | 2.5 | 2.5 | 96.6 | 3 |
| 1 | Linuron | 2.5 | 1.25 | 95.3 | 3 |
| 1 | Linuron | 0.5 | 2.5 | 94.0 | 1 |
| 1 | Linuron | 0.5 | 1.25 | 93.5 | 1 |
| 2 | Linuron | 0.5 | 1.25 | 96.6 | 1 |
| 2 | Linuron | 0.5 | 2.50 | 95.0 | 2 |
| 2 | Linuron | 2.5 | 1.25 | 96.6 | 1 |
| 2 | Linuron | 2.5 | 2.50 | 92.5 | 2 |
| 3 | Linuron | 0.5 | 1.25 | 97.5 | 2 |
| 3 | Linuron | 0.5 | 2.50 | 96.6 | 3 |
| 3 | Linuron | 2.5 | 1.25 | 94.3 | 2 |
| 3 | Linuron | 2.5 | 2.50 | 93.5 | 2 |
| 4 | Linuron | 0.5 | 1.25 | 97.5 | 1 |
| 4 | Linuron | 0.5 | 2.50 | 95.0 | 2 |
| 4 | Linuron | 2.5 | 1.25 | 96.6 | 1 |
| 4 | Linuron | 2.5 | 2.50 | 94.0 | 2 |
| 6 | Linuron | 0.5 | 1.25 | 97.5 | 1 |
| 6 | Linuron | 0.5 | 2.50 | 96.6 | 2 |
| 6 | Linuron | 2.5 | 1.25 | 96.6 | 2 |
| 6 | Linuron | 2.5 | 2.50 | 92.0 | 3 |
| 8 | Linuron | 0.5 | 1.25 | 95.0 | 2 |
| 8 | Linuron | 0.5 | 2.50 | 93.5 | 2 |
| 8 | Linuron | 2.5 | 1.25 | 94.0 | 2 |
| 8 | Linuron | 2.5 | 2.50 | 92.0 | 2 |
| 9 | Linuron | 0.5 | 1.25 | 96.6 | 1 |
| 9 | Linuron | 0.5 | 2.50 | 92.5 | 2 |
| 9 | Linuron | 2.5 | 1.25 | 96.6 | 2 |
| 9 | Linuron | 2.5 | 2.50 | 92.5 | 2 |
| 11 | Linuron | 0.5 | 1.25 | 100.0 | 1 |
| 11 | Linuron | 0.5 | 2.50 | 96.6 | 1 |
| 11 | Linuron | 2.5 | 1.25 | 96.6 | 1 |
| 11 | Linuron | 2.5 | 2.50 | 96.6 | 1 |
| 12 | Linuron | 0.5 | 1.25 | 97.5 | 1 |
| 12 | Linuron | 0.5 | 2.50 | 95.0 | 2 |
| 12 | Linuron | 2.5 | 1.25 | 96.6 | 2 |
| 12 | Linuron | 2.5 | 2.50 | 92.5 | 3 |
| 13 | Linuron | 0.5 | 1.25 | 97.5 | 1 |
| 13 | Linuron | 0.5 | 2.50 | 97.5 | 1 |
| 13 | Linuron | 2.5 | 1.25 | 97.5 | 1 |
| 13 | Linuron | 2.5 | 2.50 | 97.5 | 1 |
| 14 | Linuron | 0.5 | 1.25 | 96.6 | 1 |
| 14 | Linuron | 0.5 | 2.50 | 95.0 | 2 |
| 14 | Linuron | 2.5 | 1.25 | 95.0 | 2 |
| 14 | Linuron | 2.5 | 2.50 | 92.5 | 2 |
| 15 | Linuron | 0.5 | 1.25 | 97.5 | 1 |
| 15 | Linuron | 0.5 | 2.50 | 95.0 | 2 |
| 15 | Linuron | 2.5 | 1.25 | 95.0 | 1 |
| 15 | Linuron | 2.5 | 2.50 | 92.5 | 2 |
| 16 | Linuron | 0.5 | 1.25 | 95.0 | 2 |
| 16 | Linuron | 0.5 | 2.50 | 95.0 | 2 |
| 16 | Linuron | 2.5 | 1.25 | 95.0 | 2 |
| 16 | Linuron | 2.5 | 2.50 | 95.0 | 2 |
| 17 | Linuron | 0.5 | 1.25 | 97.5 | 1 |
| 17 | Linuron | 0.5 | 2.50 | 95.0 | 2 |
| 17 | Linuron | 2.5 | 1.25 | 95.0 | 2 |
| 17 | Linuron | 2.5 | 2.50 | 92.5 | 3 |
| 18 | Linuron | 0.5 | 1.25 | 97.5 | 1 |
| 18 | Linuron | 0.5 | 2.50 | 97.5 | 1 |
| 18 | Linuron | 2.5 | 1.25 | 95.0 | 2 |
| 18 | Linuron | 2.5 | 2.50 | 95.0 | 2 |
| 19 | Linuron | 0.5 | 1.25 | 95.0 | 2 |
| 19 | Linuron | 0.5 | 2.50 | 95.0 | 2 |
| 19 | Linuron | 2.5 | 1.25 | 92.5 | 3 |
| 19 | Linuron | 2.5 | 2.50 | 92.5 | 3 |
| 23 | Linuron | 0.5 | 1.25 | 97.5 | 1 |
| 23 | Linuron | 0.5 | 2.50 | 97.5 | 1 |
| 23 | Linuron | 2.5 | 1.25 | 97.5 | 1 |
| 23 | Linuron | 2.5 | 2.50 | 97.5 | 1 |
| 52 | Linuron | 0.5 | 1.25 | 97.5 | 1 |
| 52 | Linuron | 0.5 | 2.50 | 95.0 | 2 |
| 52 | Linuron | 2.5 | 1.25 | 96.5 | 1 |
| 52 | Linuron | 2.5 | 2.50 | 95.0 | 2 |
| CGA 43.089 | Linuron | 0.5 | 1.25 | 92.5 | 3 |
| CGA 43.089 | Linuron | 0.5 | 2.50 | 90.0 | 3 |
| CGA 43.089 | Linuron | 2.5 | 1.25 | 89.0 | 3 |
| CGA 43.089 | Linuron | 2.5 | 2.50 | 89.0 | 3 |
| — | Linuron | — | 2.0 | 88.0 | 7 |
| — | Fenuron | — | 1.0 | 90.0 | 5 |
| — | Linuron | — | 2.5 | 86.0 | 7 |
| — | Linuron | — | 1.25 | 89.0 | 5 |
| — | untreated control | — | — | 96.6 | 1 |

A known antidote, cyanomethoxy-iminophenylacetonitrile (code number: CGA 43,089: was used as reference agent in these experiments.

The data of Table III prove that the toxicity of both fenuron and linuron is diminished and the sprouting percentage of the maize is improved by using the nitrile derivatives.

EXAMPLE 39

Study of the antidote effect in the case of thiolcarbamate-type herbicides in greenhouse tests These tests were carried out in pots of 14 cm in diameter with 5-fold repetitions. The pots were filled with sandy adobe soil to the two-thirds of their volume and 10 grains of maize each were placed in the pots. Then, the grains were covered with treated or untreated, respectively soil of 5 cm in height according to the given experiment. The soil was treated in such a way that the composition containing both the antidote and herbicide as calculated for the soil with a given surface area was diluted with a water amount corresponding to 400 liters/hectare and then, this mixture was sprayed onto the soil by using a rotary, small concrete mixer. In addition to the experimental samples treated with the herbicide alone or treated, respectively with both the antidote and herbicide, an untreated control was also used.

The plants were cultivated in a greenhouse and sprinkled when necessary. The evaluation was carried out at the end of the fourth week following the sowing. The percentage of sprouting and the EWRC score were determined; furthermore, the green weight of the sprouting plant was measured and related to that of the untreated control. The results are summarized in Table IV.

TABLE IV

| Nitrile compound No. | Treatment with Antidote kg/hectare | Treatment with Herbicide EPTC kg/hectare | Sprouting % | EWRC score | Green weight % |
|---|---|---|---|---|---|
| 1 | 2.50 | — | 83.3 | 1 | 85.8 |
| 1 | 2.50 | 8.0 | 80.0 | 1 | 99.7 |
| 1 | 0.50 | 8.0 | 76.6 | 1 | 100.8 |
| 10 | 2.50 | — | 83.3 | 1 | 98.7 |
| 10 | 2.50 | 8.0 | 83.3 | 1 | 87.5 |
| 13 | 0.50 | 8.0 | 80.0 | 1 | 92.1 |
| 21 | 0.50 | 8.0 | 80.0 | 3 | 94.5 |
| 21 | 1.00 | 8.0 | 83.3 | 2 | 94.4 |
| 19 | 0.50 | 8.0 | 83.3 | 1 | 96.0 |
| 19 | 0.75 | 8.0 | 76.6 | 3 | 91.0 |
| 18 | 0.50 | 8.0 | 76.6 | 3 | 90.0 |
| 18 | 0.75 | 8.0 | 83.3 | 1 | 97.9 |
| — | — | 8.0 | 63.3 | 5 | 70.8 |
| R 25788 | 0.5 | 8.0 | 63.3 | 2 | 88.3 |
| — | — | — | 83.3 | 1 | 100.0 |

It can clearly be seen from Table IV that, on using the nitrile antidotes according to the invention, both the percentage of sprouting and the green weight became more advantageous on comparison to the known antidote N,N-diallyldichloroacetamide (R 25788).

EXAMPLE 40

Study of the antidote effect in the case of chloroacetanilide-type herbicides in greenhouse tests These tests were carried out in pots of 14 cm in diameter with 4-fold repetitions. The pots were filled with soil to the two-thirds of their volume and 10 sugar beet seeds each were sown in the pots, then covered with soil of 4 cm in height. The treatment was carried out with a tank mixture containing both the antidote and the chloroacetanilide-type herbicide.

The plants were cultivated in a greenhouse and sprinkled when necessary. The experiments were evaluated after sowing. The results are summarized in Table V.

TABLE V

| Nitrile compound No. | Treatment with Antidote kg/hectare | Treatment with Herbicide Acenit 50 EC kg/hectare | Sprouting % | EWRC % |
|---|---|---|---|---|
| 1 | 2.5 | — | 73.3 | 1 |
| 1 | 2.5 | 10 | 53.3 | 1 |
| 1 | 2.5 | 5 | 76.6 | 1 |
| 1 | 0.5 | — | 90.0 | 1 |
| 1 | 0.5 | 10 | 43.3 | 1 |
| 1 | 0.5 | 5 | 73.3 | 1 |
| 10 | 2.5 | — | 80.0 | 1 |
| 10 | 2.5 | 10 | 50.0 | 5 |
| 10 | 2.5 | 5 | 73.3 | 1 |
| 10 | 0.5 | — | 76.6 | 1 |
| 10 | 0.5 | 10 | 46.6 | 5 |
| 10 | 0.5 | 5 | 80.0 | 1 |
| 11 | 2.5 | — | 73.3 | 1 |
| 11 | 2.5 | 10 | 46.6 | 5 |
| 11 | 2.5 | 5 | 73.3 | 1 |
| 11 | 0.5 | — | 76.6 | 1 |
| 11 | 0.5 | 10 | 46.6 | 5 |
| 11 | 0.5 | 5 | 43.3 | 5 |
| 20 | 0.5 | — | 80.0 | 1 |
| 20 | 0.5 | 5 | 73.5 | 1 |
| 20 | 0.5 | 10 | 46.6 | 3 |
| 20 | 2.5 | — | 76.6 | 1 |
| 20 | 2.5 | 5 | 73.3 | 1 |
| 20 | 2.5 | 10 | 53.3 | 2 |
| 21 | 0.5 | — | 76.6 | 1 |
| 21 | 0.5 | 5 | 76.6 | 1 |
| 21 | 0.5 | 10 | 66.6 | 2 |
| 21 | 2.5 | — | 73.3 | 1 |
| 21 | 2.5 | 5 | 66.6 | 2 |
| 21 | 2.5 | 10 | 63.3 | 2 |
| 22 | 0.5 | — | 76.6 | 1 |
| 22 | 0.5 | 5 | 76.6 | 1 |
| 22 | 0.5 | 10 | 66.6 | 2 |
| 22 | 2.5 | — | 76.6 | 1 |
| 22 | 2.5 | 5 | 73.3 | 2 |
| 22 | 2.5 | 10 | 60.0 | 3 |
| 24 | 0.5 | — | 73.3 | 1 |
| 24 | 0.5 | 5 | 76.6 | 1 |
| 24 | 0.5 | 10 | 63.3 | 2 |
| 24 | 2.5 | — | 76.6 | 1 |
| 24 | 2.5 | 5 | 56.6 | 3 |
| 24 | 2.5 | 10 | 46.6 | 3 |
| 25 | 0.5 | — | 76.6 | 1 |
| 25 | 0.5 | 5 | 76.6 | 1 |
| 25 | 0.5 | 10 | 70.0 | 2 |
| 25 | 2.5 | — | 76.6 | 1 |
| 25 | 2.5 | 5 | 76.6 | 1 |
| 25 | 2.5 | 10 | 73.3 | 1 |
| 30 | 0.5 | — | 76.6 | 1 |
| 30 | 0.5 | 5 | 73.3 | 1 |
| 30 | 0.5 | 10 | 60.0 | 2 |
| 30 | 2.5 | — | 73.3 | 1 |
| 30 | 2.5 | 5 | 70.0 | 2 |
| 30 | 2.5 | 10 | 56.6 | 3 |
| 32 | 0.5 | — | 76.6 | 1 |
| 32 | 0.5 | 5 | 73.6 | 2 |
| 32 | 0.5 | 10 | 60.0 | 2 |
| 32 | 2.5 | — | 76.6 | 1 |
| 32 | 2.5 | 5 | 60.0 | 3 |
| 32 | 2.5 | 10 | 46.6 | 3 |
| 33 | 0.5 | — | 76.6 | 1 |
| 33 | 0.5 | 5 | 70.0 | 1 |
| 33 | 0.5 | 10 | 56.6 | 2 |
| 33 | 2.5 | — | 80.0 | 1 |
| 33 | 2.5 | 5 | 73.6 | 1 |
| 33 | 2.5 | 10 | 70.0 | 1 |
| 34 | 0.5 | — | 76.6 | 1 |
| 34 | 0.5 | 5 | 76.6 | 1 |
| 34 | 0.5 | 10 | 73.6 | 1 |
| 34 | 2.5 | — | 76.6 | 1 |
| 34 | 2.5 | 5 | 63.3 | 2 |
| 34 | 2.5 | 10 | 46.6 | 4 |
| 36 | 0.5 | — | 76.6 | 1 |
| 36 | 0.5 | 5 | 73.3 | 1 |
| 36 | 0.5 | 10 | 66.6 | 2 |
| 36 | 2.5 | — | 76.6 | 1 |
| 36 | 2.5 | 5 | 66.6 | 2 |

TABLE V-continued

| Nitrile compound No. | Treatment with Antidote kg/hectare | Herbicide Acenit 50 EC kg/hectare | Sprouting % | EWRC % |
|---|---|---|---|---|
| 36 | 2.5 | 10 | 53.3 | 2 |
| 37 | 0.5 | — | 76.6 | 1 |
| 37 | 0.5 | 5 | 66.6 | 2 |
| 37 | 0.5 | 10 | 50.0 | 3 |
| 37 | 2.5 | — | 76.6 | 1 |
| 37 | 2.5 | 5 | 46.6 | 3 |
| 37 | 2.5 | 10 | 43.3 | 4 |
| 39 | 0.5 | — | 76.6 | 1 |
| 39 | 0.5 | 5 | 76.6 | 1 |
| 39 | 0.5 | 10 | 66.6 | 2 |
| 39 | 2.5 | — | 76.6 | 1 |
| 39 | 2.5 | 5 | 53.3 | 3 |
| 39 | 2.5 | 10 | 53.3 | 3 |
| 40 | 0.5 | — | 76.6 | 1 |
| 40 | 0.5 | 5 | 73.3 | 1 |
| 40 | 0.5 | 10 | 56.6 | 2 |
| 40 | 2.5 | — | 80.0 | 1 |
| 40 | 2.5 | 5 | 53.3 | 2 |
| 40 | 2.5 | 10 | 46.6 | 3 |
| 41 | 0.5 | — | 76.6 | 1 |
| 41 | 0.5 | 5 | 73.3 | 1 |
| 41 | 0.5 | 10 | 60.0 | 2 |
| 41 | 2.5 | — | 73.6 | 1 |
| 41 | 2.5 | 5 | 66.6 | 2 |
| 41 | 2.5 | 10 | 43.3 | 3 |
| 42 | 0.5 | — | 76.6 | 1 |
| 42 | 0.5 | 5 | 73.3 | 1 |
| 42 | 0.5 | 10 | 66.6 | 1 |
| 42 | 2.5 | — | 73.3 | 1 |
| 42 | 2.5 | 5 | 56.6 | 2 |
| 42 | 2.5 | 10 | 46.6 | 3 |
| 43 | 0.5 | — | 76.6 | 1 |
| 43 | 0.5 | 5 | 76.6 | 1 |
| 43 | 0.5 | 10 | 63.3 | 2 |
| 43 | 2.5 | — | 76.6 | 1 |
| 43 | 2.5 | 5 | 66.6 | 1 |
| 43 | 2.5 | 10 | 53.3 | 3 |
| 44 | 0.5 | — | 76.6 | 1 |
| 44 | 0.5 | 5 | 63.3 | 2 |
| 44 | 0.5 | 10 | 43.3 | 3 |
| 44 | 2.5 | — | 70.0 | 2 |
| 44 | 2.5 | 5 | 56.6 | 3 |
| 44 | 2.5 | 10 | 40.0 | 4 |
| 45 | 0.5 | — | 76.6 | 1 |
| 45 | 0.5 | 5 | 76.6 | 1 |
| 45 | 0.5 | 10 | 76.6 | 2 |
| 45 | 2.5 | — | 76.6 | 1 |
| 45 | 2.5 | 5 | 63.3 | 2 |
| 45 | 2.5 | 10 | 50.0 | 3 |
| 46 | 0.5 | — | 80.0 | 1 |
| 46 | 0.5 | 5 | 73.3 | 1 |
| 46 | 0.5 | 10 | 60.0 | 2 |
| 46 | 2.5 | — | 70.0 | 2 |
| 46 | 2.5 | 5 | 56.6 | 3 |
| 46 | 2.5 | 10 | 43.3 | 4 |
| 47 | 0.5 | — | 73.3 | 1 |
| 47 | 0.5 | 5 | 66.6 | 2 |
| 47 | 0.5 | 10 | 43.3 | 4 |
| 47 | 2.5 | — | 66.6 | 2 |
| 47 | 2.5 | 5 | 43.3 | 4 |
| 47 | 2.5 | 10 | 43.3 | 4 |
| 48 | 0.5 | — | 76.6 | 1 |
| 48 | 0.5 | 5 | 73.3 | 1 |
| 48 | 0.5 | 10 | 56.6 | 3 |
| 48 | 2.5 | — | 76.6 | 1 |
| 48 | 2.5 | 5 | 56.6 | 3 |
| 48 | 2.5 | 10 | 43.3 | 3 |
| 49 | 0.5 | — | 76.6 | 1 |
| 49 | 0.5 | 5 | 76.6 | 1 |
| 49 | 0.5 | 10 | 73.3 | 1 |
| 49 | 2.5 | — | 76.6 | 1 |
| 49 | 2.5 | 5 | 73.3 | 1 |
| 49 | 2.5 | 10 | 70.0 | 1 |
| 50 | 0.5 | — | 76.6 | 1 |
| 50 | 0.5 | 5 | 70.0 | 1 |
| 50 | 0.5 | 10 | 56.6 | 2 |
| 50 | 2.5 | — | 73.3 | 1 |
| 50 | 2.5 | 5 | 66.6 | 2 |
| 50 | 2.5 | 10 | 53.3 | 2 |
| 51 | 0.5 | — | 76.6 | 1 |
| 51 | 0.5 | 5 | 73.3 | 1 |
| 51 | 0.5 | 10 | 60.0 | 1 |
| 51 | 2.5 | — | 76.6 | 1 |
| 51 | 2.5 | 5 | 60.0 | 1 |
| 51 | 2.5 | 10 | 46.6 | 3 |
| — | — | 10 | 0.0 | 9 |
| — | — | 5 | 10.0 | 8 |
| R 25788 | 2.5 | 10 | 10.0 | 8 |
| R 25788 | 0.5 | 5 | 36.6 | 8 |
| CGA 43.089 | 0.5 | — | 73.3 | 1 |
| CGA 43.089 | 0.5 | 5 | 46.6 | 3 |
| CGA 43.089 | 0.5 | 10 | 33.3 | 4 |
| CGA 43.089 | 2.5 | — | 66.6 | 2 |
| CGA 43.089 | 2.5 | 5 | 43.3 | 4 |
| CGA 43.089 | 2.5 | 10 | 36.6 | 5 |
| — | — | — | 76.6 | 1 |

The data of Table V show that, on the treatment with Acenit 50 EC containing 50% of acetochlor [chemically 2-chloro-2'-ethyl-6'-methyl-N-ethoxymethylacetanilide], the sugar beet sprouted to a very little extent (10%) or not at all. The sprouting was also low when the well known N,N-diallyldichloroacetamide (code number: R 25788) herbicide agent and cyanomethoxy-iminophenylacetonitrile (code number: CGA 43.089) antidote were used, whereas the phytotoxic effects of acetochlor were significantly diminished by using the nitrile compounds of the invention.

EXAMPLE 41

Study of the antidote effect in the case of urea-type herbicides by using various cultivated plants These tests were carried out in plastic pots lined with a plastic foil which were capable of receiving 800 g of soil. 400 g of air-dry field soil each were weighed in the cultivating pots. The soil had a pH value of 4.67, a cledginess of 46 according to Arany and an organic substance content of 1.97%. As test plants, 10 grains of Pi-3707 maize, 5 seeds of soy and 20 grains of wheat each were sown onto the soil in the pots. After sowing, the seeds were covered with 100 g of soil and the treatments were carried out in 4-fold repetitions. The plants were cultivated at 28±4° C. by using an illumination period lasting 16 hours. The water was daily supplied up to the total capacity.

The evaluation was carried out at the 12th day calculated from the sowing, i.e. at the 8th day calculated from the sprouting. The sprout height of the maize as well as the green weight of the soy and wheat were measured. The results are summarized in Tables VI, VII and VIII.

TABLE VI

| Nitrile compound No. | Herbicide | Treatment with Antidote kg/hectare | Herbicide kg/hectare | Maize sprout height cm |
|---|---|---|---|---|
| 1 | Isoproturon | 0.25 | 4.0 | 36.0 |
| 1 | Isoproturon | 1.0 | 4.0 | 31.5 |
| 5 | Isoproturon | 0.25 | 4.0 | 34.8 |
| 5 | Isoproturon | 1.0 | 4.0 | 36.7 |
| 7 | Isoproturon | 0.25 | 2.0 | 40.1 |
| 7 | Isoproturon | 1.0 | 2.0 | 39.3 |
| 10 | Isoproturon | 0.25 | 4.0 | 34.4 |

TABLE VI-continued

| Nitrile compound No. | Herbicide | Treatment with Antidote kg/hectare | Herbicide kg/hectare | Maize sprout height cm |
|---|---|---|---|---|
| 10 | Isoproturon | 1.0 | 4.0 | 36.1 |
| 11 | Isoproturon | 0.25 | 4.0 | 36.8 |
| 11 | Isoproturon | 1.0 | 4.0 | 36.2 |
| 13 | Isoproturon | 0.25 | 4.0 | 37.1 |
| 13 | Isoproturon | 1.0 | 4.0 | 36.0 |
| 25 | Isoproturon | 0.25 | 2.0 | 40.4 |
| 25 | Isoproturon | 1.0 | 2.0 | 37.1 |
| 26 | Isoproturon | 0.25 | 2.0 | 39.4 |
| 26 | Isoproturon | 1.0 | 2.0 | 40.3 |
| 27 | Isoproturon | 0.25 | 2.0 | 40.5 |
| 27 | Isoproturon | 1.0 | 2.0 | 36.9 |
| 27 | Isoproturon | 0.25 | 4.0 | 37.3 |
| 27 | Isoproturon | 1.0 | 4.0 | 32.7 |
| 28 | Isoproturon | 0.25 | 2.0 | 42.2 |
| 28 | Isoproturon | 1.0 | 2.0 | 39.3 |
| 28 | Isoproturon | 0.25 | 4.0 | 32.2 |
| 28 | Isoproturon | 1.0 | 4.0 | 36.4 |
| 29 | Isoproturon | 0.25 | 2.0 | 39.6 |
| 29 | Isoproturon | 1.0 | 2.0 | 35.7 |
| 29 | Isoproturon | 0.25 | 4.0 | 37.1 |
| 29 | Isoproturon | 1.0 | 4.0 | 37.4 |
| 31 | Isoproturon | 0.25 | 2.0 | 37.2 |
| 31 | Isoproturon | 1.0 | 2.0 | 41.8 |
| 35 | Isoproturon | 0.25 | 2.0 | 41.0 |
| 35 | Isoproturon | 1.0 | 2.0 | 38.4 |
| 38 | Isoproturon | 0.25 | 4.0 | 35.6 |
| 38 | Isoproturon | 1.0 | 4.0 | 32.4 |
| 53 | Isoproturon | 0.25 | 2.0 | 41.5 |
| 53 | Isoproturon | 1.0 | 2.0 | 38.0 |
| 56 | Isoproturon | 0.25 | 2.0 | 36.9 |
| 56 | Isoproturon | 1.0 | 2.0 | 40.9 |
| 57 | Isoproturon | 0.25 | 2.0 | 39.9 |
| 57 | Isoproturon | 1.0 | 2.0 | 35.6 |
| 58 | Isoproturon | 0.25 | 2.0 | 39.5 |
| 58 | Isoproturon | 1.0 | 2.0 | 40.9 |
| — | — | — | — | 36.9 |
| — | Isoproturon | — | 2.0 | 34.7 |
| — | Isoproturon | — | 4.0 | 29.6 |
| 5 | Diuron | 0.25 | 4.0 | 34.8 |
| 5 | Diuron | 1.0 | 4.0 | 30.3 |
| 7 | Diuron | 0.25 | 4.0 | 34.8 |
| 7 | Diuron | 1.0 | 4.0 | 33.5 |
| 10 | Diuron | 0.25 | 4.0 | 34.8 |
| 10 | Diuron | 1.0 | 4.0 | 31.0 |
| 28 | Diuron | 0.25 | 4.0 | 35.6 |
| 28 | Diuron | 1.0 | 4.0 | 31.1 |
| 31 | Diuron | 0.25 | 4.0 | 30.1 |
| 31 | Diuron | 1.0 | 4.0 | 34.7 |
| 53 | Diuron | 0.25 | 4.0 | 36.4 |
| 53 | Diuron | 1.0 | 4.0 | 33.9 |
| — | Diuron | — | 4.0 | 29.4 |
| 28 | Chlorbromuron | 0.25 | 2.0 | 37.4 |
| 28 | Chlorbromuron | 1.0 | 2.0 | 41.2 |
| 28 | Chlorbromuron | 0.25 | 4.0 | 43.4 |
| 28 | Chlorbromuron | 1.0 | 4.0 | 39.8 |
| 35 | Chlorbromuron | 0.25 | 2.0 | 42.3 |
| 35 | Chlorbromuron | 1.0 | 2.0 | 44.7 |
| 53 | Chlorbromuron | 0.25 | 2.0 | 39.6 |
| 53 | Chlorbromuron | 1.0 | 2.0 | 41.6 |
| 53 | Chlorbromuron | 0.25 | 4.0 | 44.4 |
| 53 | Chlorbromuron | 1.0 | 4.0 | 42.1 |
| 56 | Chlorbromuron | 0.25 | 2.0 | 43.1 |
| 56 | Chlorbromuron | 1.0 | 2.0 | 44.5 |
| 56 | Chlorbromuron | 0.25 | 4.0 | 40.8 |
| 56 | Chlorbromuron | 1.0 | 4.0 | 39.6 |
| 58 | Chlorbromuron | 0.25 | 2.0 | 43.8 |
| 58 | Chlorbromuron | 1.0 | 2.0 | 41.8 |
| 58 | Chlorbromuron | 0.25 | 4.0 | 40.0 |
| 58 | Chlorbromuron | 1.0 | 4.0 | 38.9 |
| — | Chlorbromuron | — | 2.0 | 36.9 |
| — | Chlorbromuron | — | 4.0 | 34.8 |

It can be seen from Table VI that the maize was protected from the harmful effects of the various urea-type herbicides by using the nitrile derivatives according to the invention as antidotes.

TABLE VII

| Nitrile compound No. | Herbicide | Treatment with Antidote kg/hectare | Herbicide kg/hectare | Green weight of wheat as % of the untreated control |
|---|---|---|---|---|
| 1 | Isoproturon | 0.25 | 4.0 | 82 |
| 1 | Isoproturon | 1.0 | 4.0 | 124 |
| 5 | Isoproturon | 0.25 | 4.0 | 116 |
| 5 | Isoproturon | 1.0 | 4.0 | 152 |
| 7 | Isoproturon | 0.25 | 4.0 | 124 |
| 7 | Isoproturon | 1.0 | 4.0 | 127 |
| 11 | Isoproturon | 0.25 | 4.0 | 86 |
| 11 | Isoproturon | 1.0 | 4.0 | 103 |
| 13 | Isoproturon | 0.25 | 4.0 | 100 |
| 13 | Isoproturon | 1.0 | 4.0 | 136 |
| 26 | Isoproturon | 0.25 | 4.0 | 97 |
| 26 | Isoproturon | 1.0 | 4.0 | 109 |
| 27 | Isoproturon | 0.25 | 4.0 | 123 |
| 27 | Isoproturon | 1.0 | 4.0 | 137 |
| 28 | Isoproturon | 0.25 | 4.0 | 83 |
| 28 | Isoproturon | 1.0 | 4.0 | 113 |
| 29 | Isoproturon | 0.25 | 4.0 | 101 |
| 29 | Isoproturon | 1.0 | 4.0 | 144 |
| 31 | Isoproturon | 0.25 | 4.0 | 123 |
| 31 | Isoproturon | 1.0 | 4.0 | 130 |
| 32 | Isoproturon | 0.25 | 4.0 | 193 |
| 32 | Isoproturon | 1.0 | 4.0 | 288 |
| 35 | Isoproturon | 0.25 | 4.0 | 136 |
| 35 | Isoproturon | 1.0 | 4.0 | 153 |
| 53 | Isoproturon | 0.25 | 4.0 | 182 |
| 53 | Isoproturon | 1.0 | 4.0 | 75 |
| 57 | Isoproturon | 0.25 | 4.0 | 147 |
| 57 | Isoproturon | 1.0 | 4.0 | 141 |
| 58 | Isoproturon | 0.25 | 4.0 | 136 |
| 58 | Isoproturon | 1.0 | 4.0 | 141 |
| — | Isoproturon | — | 4.0 | 78 |
| 6 | Diuron | 0.25 | 2.0 | 106 |
| 6 | Diuron | 1.0 | 2.0 | 111 |
| 25 | Diuron | 0.25 | 2.0 | 82 |
| 25 | Diuron | 1.0 | 2.0 | 107 |
| 26 | Diuron | 0.25 | 2.0 | 86 |
| 26 | Diuron | 1.0 | 2.0 | 103 |
| 28 | Diuron | 0.25 | 2.0 | 110 |
| 28 | Diuron | 1.0 | 2.0 | 65 |
| 31 | Diuron | 0.25 | 2.0 | 113 |
| 31 | Diuron | 1.0 | 2.0 | 102 |
| 32 | Diuron | 0.25 | 2.0 | 85 |
| 32 | Diuron | 1.0 | 2.0 | 100 |
| 38 | Diuron | 0.25 | 2.0 | 99 |
| 38 | Diuron | 1.0 | 2.0 | 106 |
| 53 | Diuron | 0.25 | 2.0 | 92 |
| 53 | Diuron | 1.0 | 2.0 | 107 |
| 56 | Diuron | 0.25 | 2.0 | 95 |
| 56 | Diuron | 1.0 | 2.0 | 116 |
| 57 | Diuron | 0.25 | 2.0 | 91 |
| 57 | Diuron | 1.0 | 2.0 | 146 |
| — | Diuron | — | 2.0 | 64 |
| 1 | Chlorbromuron | 0.25 | 2.0 | 91 |
| 1 | Chlorbromuron | 1.0 | 2.0 | 121 |
| 1 | Chlorbromuron | 0.25 | 4.0 | 107 |
| 1 | Chlorbromuron | 1.0 | 4.0 | 105 |
| 5 | Chlorbromuron | 0.25 | 2.0 | 89 |
| 5 | Chlorbromuron | 1.0 | 2.0 | 62 |
| 5 | Chlorbromuron | 0.25 | 4.0 | 104 |
| 5 | Chlorbromuron | 1.0 | 4.0 | 88 |
| 7 | Chlorbromuron | 0.25 | 2.0 | 181 |
| 7 | Chlorbromuron | 1.0 | 2.0 | 121 |
| 7 | Chlorbromuron | 0.25 | 4.0 | 59 |
| 7 | Chlorbromuron | 1.0 | 4.0 | 96 |
| 13 | Chlorbromuron | 0.25 | 2.0 | 67 |
| 13 | Chlorbromuron | 1.0 | 2.0 | 52 |
| 13 | Chlorbromuron | 0.25 | 4.0 | 108 |
| 13 | Chlorbromuron | 1.0 | 4.0 | 106 |
| 26 | Chlorbromuron | 0.25 | 2.0 | 112 |
| 26 | Chlorbromuron | 1.0 | 2.0 | 107 |
| 26 | Chlorbromuron | 0.25 | 4.0 | 108 |
| 26 | Chlorbromuron | 1.0 | 4.0 | 108 |
| 27 | Chlorbromuron | 0.25 | 2.0 | 113 |
| 27 | Chlorbromuron | 1.0 | 2.0 | 77 |
| 27 | Chlorbromuron | 0.25 | 4.0 | 99 |

TABLE VII-continued

| Nitrile compound No. | Herbicide | Treatment with Antidote kg/hectare | Treatment with Herbicide kg/hectare | Green weight of wheat as % of the untreated control |
|---|---|---|---|---|
| 27 | Chlorbromuron | 1.0 | 4.0 | 105 |
| 58 | Chlorbromuron | 0.25 | 2.0 | 100 |
| 58 | Chlorbromuron | 1.0 | 2.0 | 106 |
| 58 | Chlorbromuron | 0.25 | 4.0 | 134 |
| 58 | Chlorbromuron | 1.0 | 4.0 | 128 |
| 59 | Chlorbromuron | 0.25 | 2.0 | 106 |
| 59 | Chlorbromuron | 1.0 | 2.0 | 75 |
| 59 | Chlorbromuron | 0.25 | 4.0 | 141 |
| 59 | Chlorbromuron | 1.0 | 4.0 | 112 |
| — | Chlorbromuron | — | 2.0 | 60 |
| — | Chlorbromuron | — | 4.0 | 44 |

It is evident from the data of Table VII that the wheat was effectively protected from the harmful effect of various herbicidal urea derivatives such as isoproturon, diuron and chlorbromuron by using the nitrile derivatives of the invention as antidotes.

TABLE VIII

| Nitrile compound No. | Herbicide | Treatment with Antidote kg/hectare | Treatment with Herbicide kg/hectare | Green weight of soy as % of the untreated control |
|---|---|---|---|---|
| 1 | Isoproturon | 0.25 | 2.0 | 104 |
| 1 | Isoproturon | 1.0 | 2.0 | 103 |
| 25 | Isoproturon | 0.25 | 2.0 | 89 |
| 25 | Isoproturon | 1.0 | 2.0 | 111 |
| 32 | Isoproturon | 0.25 | 2.0 | 104 |
| 32 | Isoproturon | 1.0 | 2.0 | 92 |
| 56 | Isoproturon | 0.25 | 2.0 | 88 |
| 56 | Isoproturon | 1.0 | 2.0 | 111 |
| 57 | Isoproturon | 0.25 | 2.0 | 126 |
| 57 | Isoproturon | 1.0 | 2.0 | 119 |
| — | Isoproturon | — | 2.0 | 85 |
| 1 | Diuron | 0.25 | 2.0 | 86 |
| 1 | Diuron | 1.0 | 2.0 | 145 |
| 1 | Diuron | 0.25 | 4.0 | 106 |
| 1 | Diuron | 1.0 | 4.0 | 104 |
| 7 | Diuron | 0.25 | 2.0 | 99 |
| 7 | Diuron | 1.0 | 2.0 | 119 |
| 7 | Diuron | 0.25 | 4.0 | 91 |
| 7 | Diuron | 1.0 | 4.0 | 112 |
| 10 | Diuron | 0.25 | 2.0 | 116 |
| 10 | Diuron | 1.0 | 2.0 | 105 |
| 10 | Diuron | 0.25 | 4.0 | 98 |
| 10 | Diuron | 1.0 | 4.0 | 103 |
| 11 | Diuron | 0.25 | 2.0 | 106 |
| 11 | Diuron | 1.0 | 2.0 | 84 |
| 11 | Diuron | 0.25 | 4.0 | 106 |
| 11 | Diuron | 1.0 | 4.0 | 94 |
| 13 | Diuron | 0.25 | 2.0 | 118 |
| 13 | Diuron | 1.0 | 2.0 | 106 |
| 13 | Diuron | 0.25 | 4.0 | 97 |
| 13 | Diuron | 1.0 | 4.0 | 141 |
| 25 | Diuron | 0.25 | 2.0 | 100 |
| 25 | Diuron | 1.0 | 2.0 | 118 |
| 25 | Diuron | 0.25 | 4.0 | 92 |
| 25 | Diuron | 1.0 | 4.0 | 104 |
| 27 | Diuron | 0.25 | 2.0 | 123 |
| 27 | Diuron | 1.0 | 2.0 | 123 |
| 27 | Diuron | 0.25 | 4.0 | 92 |
| 27 | Diuron | 1.0 | 4.0 | 103 |
| 32 | Diuron | 0.25 | 2.0 | 119 |
| 32 | Diuron | 1.0 | 2.0 | 133 |
| 32 | Diuron | 0.25 | 4.0 | 134 |
| 32 | Diuron | 1.0 | 4.0 | 99 |
| 56 | Diuron | 0.25 | 2.0 | 124 |
| 56 | Diuron | 1.0 | 2.0 | 94 |
| 56 | Diuron | 0.25 | 4.0 | 89 |
| 56 | Diuron | 1.0 | 4.0 | 112 |
| 57 | Diuron | 0.25 | 2.0 | 169 |
| 57 | Diuron | 1.0 | 2.0 | 108 |
| 57 | Diuron | 0.25 | 4.0 | 88 |
| 57 | Diuron | 1.0 | 4.0 | 102 |
| — | Diuron | — | 2.0 | 82 |
| — | Diuron | — | 4.0 | 88 |
| 1 | Chlorbromuron | 0.25 | 2.0 | 88 |
| 1 | Chlorbromuron | 1.0 | 2.0 | 110 |
| 5 | Chlorbromuron | 0.25 | 2.0 | 108 |
| 5 | Chlorbromuron | 1.0 | 2.0 | 82 |
| 10 | Chlorbromuron | 0.25 | 2.0 | 110 |
| 10 | Chlorbromuron | 1.0 | 2.0 | 101 |
| 11 | Chlorbromuron | 0.25 | 2.0 | 102 |
| 11 | Chlorbromuron | 1.0 | 2.0 | 137 |
| 13 | Chlorbromuron | 0.25 | 2.0 | 112 |
| 13 | Chlorbromuron | 1.0 | 2.0 | 111 |
| 27 | Chlorbromuron | 0.25 | 2.0 | 131 |
| 27 | Chlorbromuron | 1.0 | 2.0 | 97 |
| 28 | Chlorbromuron | 0.25 | 2.0 | 85 |
| 28 | Chlorbromuron | 1.0 | 2.0 | 111 |
| 31 | Chlorbromuron | 0.25 | 2.0 | 122 |
| 31 | Chlorbromuron | 1.0 | 2.0 | 126 |
| 32 | Chlorbromuron | 0.25 | 2.0 | 122 |
| 32 | Chlorbromuron | 1.0 | 2.0 | 118 |
| 38 | Chlorbromuron | 0.25 | 2.0 | 111 |
| 38 | Chlorbromuron | 1.0 | 2.0 | 92 |
| 53 | Chlorbromuron | 0.25 | 2.0 | 126 |
| 53 | Chlorbromuron | 1.0 | 2.0 | 123 |
| 56 | Chlorbromuron | 0.25 | 2.0 | 135 |
| 56 | Chlorbromuron | 1.0 | 2.0 | 102 |
| 57 | Chlorbromuron | 0.25 | 2.0 | 137 |
| 57 | Chlorbromuron | 1.0 | 2.0 | 116 |
| — | Chlorbromuron | — | 2.0 | 80 |

The results summarized in Table VIII also support that the soy was effectively protected from the harmful effect of various herbicidal urea derivatives such as isoproturor, diuron and chlorbromuron by using the nitrile derivatives of the invention as antidotes.

EXAMPLE 42

Study of the antidote effect in the case of urea-type herbicides on maize species with various sensitivity These tests were carried cut in pots of 14 cm in diameter with 5-fold repetitions. The pots were filled with a sandy adobe soil to the two-thirds of their volume and 10 grains of maize each of the species ETA-TC, Pi-3901, Pi-3965 and Pi-3839, respectively were sown in the pots, then the grains were covered with a treated or untreated soil of 5 cm in height according to the given experiment.

The soil was treated with 6 kg/hectare of linuron together with various amounts of the nitrile antidotes. The height of the sprout was determined and compared to the untreated control. The results are summarized in Table IX.

TABLE IX

| Nitrile compound No. | Antidote dose kg/hectare | Maize species | Sprout height as % of the untreated control |
|---|---|---|---|
| 1 | 0.1 | Pi-3901 | 84.0 |
| 1 | 0.5 | Pi-3901 | 89.9 |
| 1 | 1.0 | Pi-3901 | 99.3 |
| 1 | 1.5 | Pi-3901 | 89.2 |
| 7 | 0.1 | Pi-3901 | 85.7 |
| 7 | 0.5 | Pi-3901 | 94.4 |
| 7 | 1.0 | Pi-3901 | 101.7 |
| 7 | 1.5 | Pi-3901 | 97.2 |
| 10 | 0.1 | Pi-3901 | 90.2 |
| 10 | 0.5 | Pi-3901 | 86.8 |
| 10 | 1.0 | Pi-3901 | 91.8 |
| 10 | 1.5 | Pi-3901 | 91.6 |

TABLE IX-continued

| Nitrile compound No. | Antidote dose kg/hectare | Maize species | Sprout height as % of the untreated control |
|---|---|---|---|
| 13 | 0.1 | Pi-3901 | 96.1 |
| 13 | 0.5 | Pi-3901 | 106.3 |
| 13 | 1.0 | Pi-3901 | 94.4 |
| 13 | 1.5 | Pi-3901 | 84.7 |
| 18 | 0.1 | Pi-3901 | 85.4 |
| 18 | 0.5 | Pi-3901 | 104.2 |
| 18 | 1.0 | Pi-3901 | 114.3 |
| 18 | 1.5 | Pi-3901 | 99.3 |
| — | — | Pi-3901 | 81.5 |
| 6 | 0.1 | ETA-TC | 98.8 |
| 6 | 0.5 | ETA-TC | 100.8 |
| 6 | 1.0 | ETA-TC | 89.2 |
| 6 | 1.5 | ETA-TC | 93.0 |
| 7 | 0.1 | ETA-TC | 101.4 |
| 7 | 0.5 | ETA-TC | 89.6 |
| 7 | 1.0 | ETA-TC | 94.8 |
| 7 | 1.5 | ETA-TC | 94.7 |
| 13 | 0.1 | ETA-TC | 98.0 |
| 13 | 0.5 | ETA-TC | 101.4 |
| 13 | 1.0 | ETA-TC | 97.3 |
| 13 | 1.5 | ETA-TC | 91.4 |
| — | — | ETA-TC | 89.1 |
| 1 | 0.1 | Pi-3965 | 106.8 |
| 1 | 0.5 | Pi-3965 | 98.9 |
| 1 | 1.0 | Pi-3965 | 112.9 |
| 1 | 1.5 | Pi-3965 | 109.0 |
| 6 | 0.1 | Pi-3965 | 111.5 |
| 6 | 0.5 | Pi-3965 | 97.5 |
| 6 | 1.0 | Pi-3965 | 96.1 |
| 6 | 1.5 | Pi-3965 | 109.3 |
| 7 | 0.1 | Pi-3965 | 100.5 |
| 7 | 0.5 | Pi-3965 | 119.7 |
| 7 | 1.0 | Pi-3965 | 97.5 |
| 7 | 1.5 | Pi-3965 | 117.2 |
| 10 | 0.1 | Pi-3965 | 111.1 |
| 10 | 0.5 | Pi-3965 | 118.3 |
| 10 | 1.0 | Pi-3965 | 121.5 |
| 10 | 1.5 | Pi-3965 | 101.4 |
| 13 | 0.1 | Pi-3965 | 107.9 |
| 13 | 0.5 | Pi-3965 | 112.2 |
| 13 | 1.0 | Pi-3965 | 121.9 |
| 13 | 1.5 | Pi-3965 | 109.0 |
| 18 | 0.1 | Pi-3965 | 120.4 |
| 18 | 0.5 | Pi-3965 | 101.1 |
| 18 | 1.0 | Pi-3965 | 96.4 |
| 18 | 1.5 | Pi-3965 | 97.8 |
| — | — | Pi-3965 | 96.1 |
| 1 | 0.1 | Pi-3839 | 79.5 |
| 1 | 0.5 | Pi-3839 | 86.8 |
| 1 | 1.0 | Pi-3839 | 96.0 |
| 1 | 1.5 | Pi-3839 | 86.2 |
| 3 | 0.1 | Pi-3839 | 111.6 |
| 3 | 0.5 | Pi-3839 | 104.2 |
| 3 | 1.0 | Pi-3839 | 106.8 |
| 3 | 1.5 | Pi-3839 | 104.8 |
| 7 | 0.1 | Pi-3839 | 94.2 |
| 7 | 0.5 | Pi-3839 | 87.8 |
| 7 | 1.0 | Pi-3839 | 84.9 |
| 7 | 1.5 | Pi-3839 | 92.6 |
| 10 | 0.1 | Pi-3839 | 92.4 |
| 10 | 0.5 | Pi-3839 | 96.8 |
| 10 | 1.0 | Pi-3839 | 92.3 |
| 10 | 1.5 | Pi-3839 | 97.1 |
| 13 | 0.1 | Pi-3839 | 100.3 |
| 13 | 0.5 | Pi-3839 | 90.0 |
| 13 | 1.0 | Pi-3839 | 97.4 |
| 13 | 1.5 | Pi-3839 | 89.1 |
| 18 | 0.1 | Pi-3839 | 96.1 |
| 18 | 0.5 | Pi-3839 | 105.6 |
| 18 | 1.0 | Pi-3839 | 105.1 |
| 18 | 1.5 | Pi-3839 | 103.9 |
| — | — | Pi-3839 | 78.5 |

It can be seen from Table IX that maize species with various sensitivity were also protected by using the antidotes of the invention.

After the greenhouse tests, the phytotoxicity-diminishing effect of the nitrile derivatives according to the invention was investigated in small-parcel experiments.

In these tests, the antidote and herbicide compositions were used partly in the form of a tank mixture and partly in a formulation containing both the herbicide agent and the nitrile derivative.

The experiments were continuously evaluated by determining the percentage of sprouting of the cultivated plants, by observing the damages caused by the herbicides as well as by evaluating the amount of the crop and registering the herbicide action. From an economical point of view, the water content of the crop has a high significance: this water content is increased on the use of herbicides. Thus, on the assessment of our field experiments, a real extent of the antidote action also appears in the decrease of the water content.

EXAMPLE 43

Study of the antidote effect in the case of urea-type herbicides in small-parcel tests The phytotoxicity-decreasing effect in the case of an urea-type herbicide was studied with pivalonitrile (compound No. 1) in small-parcel tests. The antidote was formulated together with linuron as active ingredient in a common formulation according to four ratios. The formulation was applied by spraying with water in the form of a wettable powder composition (as described in Example 15).

These tests were carried out on parcels of 20 m² with 4-fold repetitions by using Pioner-3950 maize cultivated on an adobe soil of Mezőség containing 1.46% of organic substances.

The results of the measurements, i.e. the number of plants/parcel, the height of the plants, the length of the maize-ear covered by grains, the amount of grain-crop/parcel and the water content of the harvested crop are summarized in Table X.

TABLE X

| Nitrile No. | compound Dose kg/hectare | Linuron Dose kg/hectare | No. of plants pc. | Plant height cm | Maize-ear covered with grains cm | Crop amount kg | Water content % |
|---|---|---|---|---|---|---|---|
| 1 | 0.5 | 4 | 150 | 186.7 | 17.3 | 6.95 | 29.4 |
| 1 | 0.5 | 2 | 148 | 194.5 | 16.3 | 6.66 | 30.2 |
| 1 | 0.25 | 4 | 147 | 178.2 | 16.4 | 6.37 | 30.4 |
| 1 | 0.25 | 2 | 147 | 186.2 | 15.0 | 5.49 | 28.2 |
| — | — | 4 | 140 | 172.5 | 15.1 | 4.45 | 31.7 |
| — | — | 2 | 142 | 178.4 | 15.6 | 4.80 | 31.0 |

TABLE X-continued

| Nitrile No. | compound Dose kg/hectare | Linuron Dose kg/hectare | No. of plants pc. | Plant height cm | Maize-ear covered with grains cm | Crop amount kg | Water content % |
|---|---|---|---|---|---|---|---|
| | untreated control | | 151 | 196.1 | 15.8 | 5.98 | 28.3 |

Simultaneously, the occurrence of seven weeds in these parcels was investigated and the extent of the weed control was characterized by EWRC scoring in Table XI.

The weeds investigated were as follows:
1: *Echinochloa crusgalli;*
2: *Amaranthus chlorostachis;*
3: *Chenopodium album;*
4: *Polygonum lopathiofolium;*
5: *Equisetum arvense;*
6: *Chenopodium hybridum;*
7: *Setaria glauca*

TABLE XI

| Nitrile compound Dose kg/hectare | Linuron Dose kg/hectare | Time of evaluation | Herbicide effect in EWRC score | | | | | | |
|---|---|---|---|---|---|---|---|---|---|
| No. | | | | 1 | 2 | 3 | 4 | 5 | 6 | 7 |
| 1 | 0.5 | 4 | 01.06. | 1 | 1 | 1 | 1 | 1 | 1 | 1 |
| | | | 04.07. | 1 | 1 | 1 | 3 | 3 | 1 | 1 |
| | | | 06.08. | 2 | 1 | 1 | 6 | 7 | 1 | 1 |
| 1 | 0.5 | 2 | 01.06. | 1 | 1 | 1 | 1 | 1 | 1 | 1 |
| | | | 04.07. | 1 | 1 | 1 | 4 | 3 | 1 | 1 |
| | | | 06.08. | 2 | 1 | 1 | 6 | 7 | 1 | 1 |
| 1 | 0.25 | 4 | 01.06. | 1 | 1 | 1 | 1 | 1 | 1 | 1 |
| | | | 04.07. | 1 | 1 | 1 | 3 | 4 | 1 | 1 |
| | | | 06.08. | 2 | 1 | 1 | 6 | 7 | 1 | 1 |
| 1 | 0.25 | 2 | 01.06. | 1 | 1 | 1 | 1 | 1 | 1 | 1 |
| | | | 04.07. | 1 | 1 | 1 | 3 | 3 | 1 | 1 |
| | | | 06.08. | 2 | 1 | 1 | 6 | 7 | 1 | 1 |
| — | — | 4 | 01.06. | 1 | 1 | 1 | 1 | 1 | 1 | 1 |
| | | | 04.07. | 1 | 1 | 1 | 2 | 3 | 1 | 1 |
| | | | 06.08. | 1 | 1 | 1 | 5 | 5 | 1 | 1 |
| — | — | 2 | 01.06. | 1 | 1 | 1 | 1 | 1 | 1 | 1 |
| | | | 04.07. | 1 | 1 | 1 | 3 | 3 | 1 | 1 |
| | | | 06.08. | 2 | 1 | 1 | 6 | 7 | 1 | 1 |
| untreated control | | | 01.06. | 9 | 8 | 7 | 8 | 8 | 7 | 8 |
| | | | 04.07. | 9 | 9 | 8 | 9 | 9 | 8 | 9 |
| untreated control | | | 06.08. | 9 | 9 | 9 | 9 | 9 | 8 | 9 |

It is evident from Table XI, that the herbicide effect of linuron was not decreased, whereas the phytotoxicity exerted or the maize was eliminated by using the antidote of the invention.

EXAMPLE 44

Similarly to the preceding Example, the diminishing effect of the nitrile derivatives of the invention on the phytotoxicity of the commonly known thiolcarbamate (EPTC) herbicide as well as the development of the herbicide action were investigated in small-parcel field experiments.

The tests were carried out in parcels of 20 m² by cultivating NK-PI-20 maize in 4-fold repetitions.

For the treatments, EPTC and two nitrile derivatives (compounds Nos. 1 and 11) were applied by spraying with water before sowing in the form of an emulsifiable concentrate as described in Example 13 and 14 and worked into the soil. The results of these experiments are summarized in Table XII.

TABLE XII

| Nitrile antidote No. | Dose kg/hectare | EPTC Dose kg/hectare | No. of plants pc | Plant height cm | Maize-ear covered with grains cm | Crop amount kg | Water content % |
|---|---|---|---|---|---|---|---|
| 1 | 1.25 | 8 | 167 | 192.1 | 21.8 | 8.27 | 24.8 |
| 1 | 0.25 | 8 | 158 | 185.3 | 22.8 | 6.15 | 30.4 |
| 11 | 1.25 | 8 | 163 | 187.2 | 21.6 | 5.85 | 25.8 |
| 11 | 0.25 | 8 | 157 | 182.6 | 20.5 | 7.60 | 31.7 |
| — | — | 8 | 145 | 171.6 | 19.9 | 5.12 | 33.6 |
| R-25788 | 1.25 | 8 | 160 | 186.1 | 21.4 | 5.71 | 33.6 |
| untreated control | | | 165 | 188.7 | 20.4 | 6.63 | 29.2 |

Likewise, the herbicide effect was also studied in the parcels by using the EWRC scores. The results are summarized in Table XIII.

TABLE XIII

| Nitrile antidote No. | Dose kg/hectare | EPTC Dose kg/hectare | Time of evaluation | Herbicide effect in EWRC score | | | | | | |
|---|---|---|---|---|---|---|---|---|---|---|
| | | | | 1 | 2 | 3 | 4 | 5 | 6 | 7 |
| 1 | 1.25 | 8 | 11.06 | 1 | 1 | 1 | 2 | 3 | 1 | 1 |
| | | | 13.07. | 1 | 1 | 1 | 5 | 6 | 1 | 1 |
| | | | 12.08. | 1 | 1 | 1 | 7 | 8 | 1 | 1 |
| 1 | 0.25 | 8 | 11.06. | 1 | 1 | 1 | 2 | 2 | 1 | 1 |
| | | | 13.07. | 1 | 1 | 1 | 6 | 6 | 1 | 1 |
| | | | 12.08. | 1 | 1 | 1 | 7 | 8 | 1 | 1 |
| 11 | 1.25 | 8 | 11.06 | 1 | 1 | 1 | 2 | 2 | 1 | 1 |
| | | | 13.07. | 1 | 1 | 1 | 5 | 5 | 1 | 1 |
| | | | 12.08. | 1 | 1 | 1 | 7 | 8 | 1 | 1 |
| 11 | 0.25 | 8 | 11.06. | 1 | 1 | 1 | 2 | 2 | 1 | 1 |

TABLE XIII-continued

| Nitrile antidote | | EPTC | | Herbicide effect in EWRC score | | | | | | |
|---|---|---|---|---|---|---|---|---|---|---|
| No. | Dose kg/hectare | Dose kg/hectare | Time of evaluation | 1 | 2 | 3 | 4 | 5 | 6 | 7 |
| | | | 13.07. | 1 | 1 | 1 | 6 | 5 | 1 | 1 |
| | | | 12.08. | 1 | 1 | 1 | 7 | 8 | 1 | 1 |
| — | — | 8 | 11.06. | 1 | 1 | 1 | 2 | 3 | 1 | 1 |
| | | | 13.07. | 1 | 1 | 1 | 4 | 6 | 1 | 1 |
| | | | 12.08. | 1 | 1 | 1 | 5 | 8 | 1 | 1 |
| R-25788 | 1.25 | 8 | 11.06. | 1 | 1 | 1 | 2 | 2 | 1 | 1 |
| | | | 13.07. | 1 | 1 | 1 | 4 | 5 | 1 | 1 |
| | | | 12.08. | 1 | 1 | 1 | 6 | 8 | 1 | 1 |
| untreated control | | | 11.06. | 8 | 7 | 7 | 8 | 8 | 6 | 7 |
| | | | 13.07. | 9 | 8 | 8 | 9 | 9 | 7 | 8 |
| | | | 12.08. | 9 | 8 | 9 | 9 | 9 | 7 | 8 |

EXAMPLE 45

Study of the antidote effect in the case of a chlortoluron herbicide in small-parcel experiment The antidote effect of the compounds according to the invention was studied in a small-parcel field experiment on a wheat of Rana 2 species.

These experiments were carried out in parcels of 20 m² on a loose sandy soil with 4-fold repetitions.

The treatments were performed by spraying out an appropriate amount of the antidote and herbicide in the form of a tank mixture in the middle of March.

The evaluation was made by using an EWRC score, twice during the cultivating period. Both the damages caused by the herbicide as well as the herbicide effect were determined. The results are summarized in Table XIV.

TABLE XIV

| Nitrile compound | | Chlortoluron 80 WP | EWRC score | | | |
|---|---|---|---|---|---|---|
| | | | Wheat | | Apera spica venti | |
| No. | Dose kg/ hectare | Dose kg/ hectare | 1 | 2 | 1 | 2 |
| — | — | 2.0 | 1 | 1 | 1 | 1 |
| — | — | 4.0 | 4 | 3 | 1 | 1 |
| — | — | 6.0 | 6 | 5 | 1 | 1 |
| 1 | 0.2 | 2.0 | 1 | 1 | 1 | 1 |
| 1 | 0.4 | 2.0 | 1 | 1 | 1 | 1 |
| 1 | 0.4 | 4.0 | 1 | 1 | 1 | 1 |
| 1 | 0.8 | 4.0 | 1 | 1 | 1 | 1 |
| 1 | 0.6 | 6.0 | 2 | 1 | 1 | 1 |
| 1 | 1.2 | 6.0 | 1 | 1 | 1 | 1 |
| 11 | 0.2 | 2.0 | 1 | 1 | 1 | 1 |
| 11 | 0.4 | 2.0 | 1 | 1 | 1 | 1 |
| 11 | 0.4 | 4.0 | 1 | 1 | 1 | 1 |
| 11 | 0.8 | 4.0 | 1 | 1 | 1 | 1 |
| 11 | 0.6 | 6.0 | 2 | 1 | 1 | 1 |
| 11 | 1.2 | 6.0 | 2 | 1 | 1 | 1 |
| 23 | 0.2 | 2.0 | 1 | 1 | 1 | 1 |
| 23 | 0.4 | 2.0 | 1 | 1 | 1 | 1 |
| 23 | 0.4 | 4.0 | 1 | 1 | 1 | 1 |
| 23 | 0.8 | 4.0 | 1 | 1 | 2 | 2 |
| 23 | 0.6 | 6.0 | 1 | 1 | 1 | 1 |
| 23 | 1.2 | 6.0 | 1 | 1 | 2 | 3 |
| 23 | 0.2 | 2.0 | 1 | 1 | 1 | 1 |
| 25 | 0.4 | 2.0 | 1 | 1 | 1 | 1 |
| 25 | 0.4 | 4.0 | 2 | 2 | 1 | 1 |
| 25 | 0.8 | 4.0 | 2 | 1 | 1 | 1 |
| 25 | 0.6 | 6.0 | 3 | 2 | 1 | 1 |
| 25 | 1.2 | 6.0 | 3 | 1 | 1 | 1 |
| 30 | 0.2 | 2.0 | 1 | 1 | 1 | 1 |
| 30 | 0.4 | 2.0 | 1 | 1 | 1 | 1 |
| 30 | 0.4 | 4.0 | 2 | 1 | 1 | 1 |
| 30 | 0.8 | 4.0 | 2 | 2 | 1 | 1 |
| 30 | 0.6 | 6.0 | 3 | 2 | 1 | 1 |
| 30 | 1.2 | 6.0 | 3 | 1 | 1 | 1 |
| 41 | 0.2 | 2.0 | 1 | 1 | 1 | 1 |
| 41 | 0.4 | 2.0 | 1 | 1 | 1 | 1 |
| 41 | 0.4 | 4.0 | 3 | 2 | 1 | 1 |
| 41 | 0.8 | 4.0 | 2 | 1 | 1 | 1 |
| 41 | 0.6 | 6.0 | 3 | 2 | 1 | 1 |
| 41 | 1.2 | 6.0 | 2 | 1 | 1 | 1 |
| CGA.43.089 | 0.2 | 2.0 | 1 | 1 | 1 | 1 |
| CGA 43.089 | 0.4 | 2.0 | 1 | 1 | 1 | 1 |
| CGA 43.089 | 0.4 | 4.0 | 3 | 2 | 1 | 1 |
| CGA 43.089 | 0.8 | 4.0 | 3 | 2 | 1 | 1 |
| CGA 43.089 | 0.6 | 6.0 | 5 | 4 | 1 | 1 |
| CGA 43.089 | 1.2 | 6.0 | 4 | 3 | 1 | 1 |

It is evident from the data of Table XIV that, in comparison to cyanomethoxy-iminophenylacetonitrile (code number: 43.089), a known antidote, the antidote nitrile derivatives of the invention were more effective in the decrease or elimination, respectively of the harmful effect of the chlortoluron herbicide.

EXAMPLE 46

Study of the antidote effect in the case of a metobromuron herbicide in small-parcel experiment The antidote effect of the compounds according to the invention was studied in a small-parcel field experiment on a potato of Desirée species.

These experiments were carried out in parcels of 20 m² on a loose sandy soil with 4-fold repetitions.

The treatments were postemergently carried out after hilling. The evaluation was performed by using an EWRC score, twice during the cultivating period. Both the damages caused by the herbicide as well as the herbicide effect were determined. The results are summarized in Table XV.

TABLE XV

| Nitrile compound | | Metobromuron 50 WP | EWRC score | | | | | |
|---|---|---|---|---|---|---|---|---|
| | | | Potato | | Echinocloa | | Setaria | |
| No. | Dose kg/ hectare | Dose kg/ hectare | 1 | 2 | 1 | 2 | 1 | 2 |
| — | — | 3.0 | 1 | 1 | 2 | 3 | 2 | 2 |
| — | — | 6.0 | 4 | 2 | 1 | 1 | 1 | 1 |
| — | — | 9.0 | 6 | 2 | 1 | 1 | 1 | 1 |
| 5 | 0.15 | 3.0 | 1 | 1 | 2 | 3 | 2 | 2 |
| 5 | 0.30 | 3.0 | 1 | 1 | 2 | 3 | 2 | 2 |
| 5 | 0.30 | 6.0 | 2 | 1 | 1 | 1 | 1 | 1 |
| 5 | 0.60 | 6.0 | 1 | 1 | 1 | 1 | 1 | 1 |
| 5 | 0.45 | 9.0 | 2 | 2 | 1 | 1 | 1 | 1 |
| 5 | 0.90 | 9.0 | 1 | 1 | 1 | 1 | 1 | 1 |

TABLE XV-continued

| Nitrile compound | | Meto-bromuron 50 WP Dose kg/hectare | EWRC score | | | | | |
|---|---|---|---|---|---|---|---|---|
| | | | Potato | | Echinocloa | | Setaria | |
| No. | Dose kg/hectare | | 1 | 2 | 1 | 2 | 1 | 2 |
| 20 | 0.15 | 3.0 | 1 | 1 | 2 | 3 | 2 | 2 |
| 20 | 0.30 | 3.0 | 1 | 1 | 2 | 3 | 2 | 3 |
| 20 | 0.30 | 6.0 | 3 | 2 | 1 | 1 | 1 | 1 |
| 20 | 0.60 | 6.0 | 2 | 1 | 1 | 1 | 1 | 1 |
| 20 | 0.45 | 9.0 | 3 | 2 | 1 | 1 | 1 | 1 |
| 20 | 0.90 | 9.0 | 2 | 1 | 1 | 1 | 1 | 1 |
| 28 | 0.15 | 3.0 | 1 | 1 | 2 | 3 | 2 | 2 |
| 28 | 0.30 | 3.0 | 1 | 1 | 2 | 3 | 2 | 3 |
| 28 | 0.30 | 6.0 | 2 | 2 | 1 | 1 | 1 | 1 |
| 28 | 0.60 | 6.0 | 2 | 1 | 1 | 1 | 1 | 1 |
| 28 | 0.45 | 9.0 | 3 | 2 | 1 | 1 | 1 | 1 |
| 28 | 0.90 | 9.0 | 2 | 1 | 1 | 1 | 1 | 1 |
| CGA 43.089 | 0.15 | 3.0 | 1 | 1 | 2 | 3 | 2 | 2 |
| CGA 43.089 | 0.30 | 3.0 | 1 | 1 | 2 | 3 | 2 | 2 |
| CGA 43.089 | 0.30 | 6.0 | 3 | 2 | 1 | 1 | 1 | 1 |
| CGA 43.089 | 0.60 | 6.0 | 3 | 2 | 1 | 1 | 1 | 1 |
| CGA 43.089 | 0.45 | 9.0 | 5 | 2 | 1 | 1 | 1 | 1 |
| CGA 43.089 | 0.90 | 9.0 | 4 | 2 | 1 | 1 | 1 | 1 |

It is evident from the data of Table XV that, in comparison to cyanomethoxy-iminophenylacetonitrile (code number: 43.089:, a known antidote, the antidote nitrile derivatives of the invention were more effective in the decrease or elimination, respectively of the harmful effect of the metobromuron herbicide.

EXAMPLE 47

Study of the antidote effect in the case of a chlorbormuron herbicide in small-parcel experiment This field experiment was carried out or sun-flower of NSA-26 species in parcels of 20 m² with 4-fold repetitions on a mildly humified soil containing 1% of organic materials.

The treatments were performed preemergently by applying the antidote and herbicide in the form of a tank mixture. In the experimental area no weediness was developed thus, the phytotoxic effect caused by the herbicide was only evaluated. The results are summarized in Table XVI.

TABLE XVI

| Nitrile compound | | Chlorbromuron 50 WP Dose kg/hectare | EWRC score | |
|---|---|---|---|---|
| No. | Dose kg/hectare | | 1 | 2 |
| | | 2.5 | 2 | 1 |
| | | 7.5 | 6 | 5 |
| 33 | 0.1 | 2.5 | 2 | 1 |
| 33 | 0.3 | 2.5 | 1 | 1 |
| 33 | 0.3 | 7.5 | 4 | 2 |
| 33 | 0.9 | 7.5 | 3 | 2 |
| 35 | 0.1 | 2.5 | 2 | 1 |
| 35 | 0.3 | 2.5 | 1 | 1 |
| 35 | 0.3 | 7.5 | 3 | 3 |
| 35 | 0.9 | 7.5 | 3 | 2 |
| 40 | 0.1 | 2.5 | 2 | 1 |
| 40 | 0.3 | 2.5 | 1 | 1 |
| 40 | 0.3 | 7.5 | 3 | 3 |
| 40 | 0.9 | 7.5 | 3 | 3 |
| 42 | 0.1 | 2.5 | 1 | 1 |
| 42 | 0.3 | 2.5 | 1 | 1 |
| 42 | 0.3 | 7.5 | 2 | 1 |
| 42 | 0.9 | 7.5 | 1 | 1 |
| 44 | 0.1 | 2.5 | 2 | 1 |
| 44 | 0.3 | 2.5 | 1 | 1 |
| 44 | 0.3 | 7.5 | 3 | 1 |
| 44 | 0.9 | 7.5 | 2 | 1 |

TABLE XVI-continued

| Nitrile compound | | Chlorbromuron 50 WP Dose kg/hectare | EWRC score | |
|---|---|---|---|---|
| No. | Dose kg/hectare | | 1 | 2 |
| 48 | 0.1 | 2.5 | 1 | 1 |
| 48 | 0.3 | 2.5 | 1 | 1 |
| 48 | 0.3 | 7.5 | 3 | 1 |
| 48 | 0.9 | 7.5 | 2 | 1 |
| 49 | 0.1 | 2.5 | 1 | 1 |
| 49 | 0.3 | 2.5 | 1 | 1 |
| 49 | 0.3 | 7.5 | 2 | 1 |
| 49 | 0.9 | 7.5 | 1 | 1 |
| 51 | 0.1 | 2.5 | 2 | 1 |
| 51 | 0.3 | 2.5 | 1 | 1 |
| 51 | 0.3 | 7.5 | 2 | 2 |
| 51 | 0.9 | 7.5 | 2 | 2 |
| GCA 43.089 | 0.1 | 2.5 | 2 | 1 |
| CGA 43.089 | 0.3 | 2.5 | 2 | 1 |
| CGA 43.089 | 0.3 | 7.5 | 4 | 3 |
| CGA 43.089 | 0.9 | 7.5 | 4 | 3 |

The results of Table XVI also support that, in comparison to cyanomethoxy-iminophenylacetonitrile (code number: 43.089) a known antidote, the antidote according to the invention showed a better protective action.

We claim:

1. An herbicide composition containing a nitrile derivative as antidote which comprises as herbicidally active ingredient an urea derivative of the formula (II)

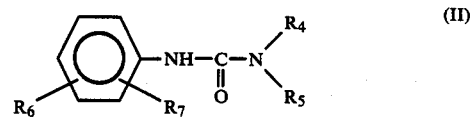

wherein
$R_4$ and $R_5$ which are the same or different, stand for a methyl or methoxy group; and
$R_6$ and $R_7$ which are the same or different, represent hydrogen, halogen, a $C_{1-3}$ alkyl or a methoxy group, together with a nitrile derivative of the formula (I),

wherein
$R_1$ and $R_2$ which are the same or different, stand for hydrogen or a methyl, ethyl, allyl, phenyl or benzyl group;
$R_1$ and $R_2$ together may stand for a benzylidene group; and $R_3$ means a methyl, phenyl, chlorophenyl, or lower alkoxyphenyl group in a mass ratio from 40:1 to 1:2 of the herbicidally active ingredient to the antidote nitrile derivative, together with an agriculturally acceptable inert carrier.

2. An herbicidal composition as defined in claim 1 wherein the mass ratio is from 40:1 to 1:1 of the herbicidally active ingredient to the antidote nitrile derivative.

3. A herbicide composition as claimed in claim 1 which comprises as herbicidally active ingredient an urea derivative of the formula (II), wherein
- $R_4$ and $R_5$ which are the same or different, stand for a methyl or methoxy group; and
- $R_6$ and $R_7$ which are the same or different, represent hydrogen, halogen, a methyl or a methoxy group together with a nitrile derivative as antidote.

4. The herbicidal composition defined in claim 1 which comprises as herbicidally active ingredient a compound of the Formula (II) and a compound of the Formula (I) as the herbicidal antidote in a weight ratio of 10:1 to 1:2.

5. The herbicidal composition defined in claim 4 which comprises as the compound of the Formula (II) in Linuron and the compound of the Formula (I) is 2-allyl-2-phenyl-4-pentene-nitrile in a weight ratio of 5:1 to 1:2.

* * * * *